(12) United States Patent
Chern et al.

(10) Patent No.: US 7,129,359 B2
(45) Date of Patent: Oct. 31, 2006

(54) IMIDAZOLIDINONE COMPOUNDS

(75) Inventors: Jyh-Haur Chern, Taipei (TW);
Shin-Ru Shih, Tao-Yuan (TW);
Chiung-Tong Chen, Taipei (TW);
Chih-Shiang Chang, Lujhom (TW);
Chung-Chi Lee, Chung-He (TW);
Yen-Chun Lee, Taitung County (TW);
Chia-Liang Tai, Hsinchu (TW)

(73) Assignee: National Health Research Institutes, Taipei (TW)

( * ) Notice: Subject to any disclaimer, the term of this patent is extended or adjusted under 35 U.S.C. 154(b) by 420 days.

(21) Appl. No.: 10/717,786

(22) Filed: Nov. 19, 2003

(65) Prior Publication Data

US 2004/0116476 A1   Jun. 17, 2004

Related U.S. Application Data

(63) Continuation-in-part of application No. 10/191,941, filed on Jul. 9, 2002, now Pat. No. 6,706,739.

(51) Int. Cl.
*C07D 401/04* (2006.01)
*C07D 233/02* (2006.01)
*A61K 31/44* (2006.01)
*A61K 31/4166* (2006.01)

(52) U.S. Cl. ............................. 546/274.4; 546/268.1; 546/272.7; 546/274.1; 548/300.1; 548/311.1; 548/314.7; 514/336; 514/341; 514/396

(58) Field of Classification Search ............ 546/268.1, 546/272.7, 269.1, 274.1, 274.4; 548/300.1, 548/311.1, 314.7; 514/336, 341, 396, 398
See application file for complete search history.

(56) References Cited

U.S. PATENT DOCUMENTS 5,464,848 A    11/1995    Diana et al. ............... 514/364
6,706,739 B1 *  3/2004    Shia et al. ................. 514/341

OTHER PUBLICATIONS

Kak-Shan Shia, et al. "Design Synthesis, and Structure-Activity Relationship of Pyridyl Imidazolidinones: A Novel Class of Potent and Selective Human Enterovirus 71 Inhibitors" pp. 1644-1655 Mar. 13, 2002 Published on web.

* cited by examiner

*Primary Examiner*—Golam M. M. Shameem

(74) *Attorney, Agent, or Firm*—Fish & Richardson P.C.

(57) ABSTRACT

This invention relates to compounds of the following formula:

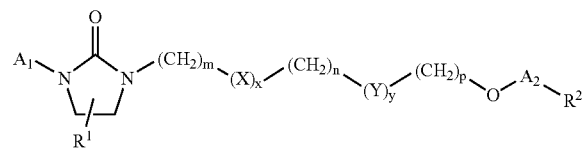

in which $R^1$, $R^2$, $A_1$, $A_2$, X, Y, m, n, p, x and y are as defined herein, pharmaceutical compositions comprising the compounds and use of the compounds in treating enterovirus infection.

41 Claims, No Drawings

IMIDAZOLIDINONE COMPOUNDS

RELATED APPLICATION

This application is a continuation-in-part of, and claims priority to U.S. application Ser. No. 10/191,941, filed on Jul. 9, 2002, now U.S. Pat No. 6,706,739 the contents of which are incorporated herein by reference.

BACKGROUND

The Picornaviridae family includes about 70 distinct serotypes of enterovirus. Clinical manifestations of enterovirus infection range from mild "summer cold" to neurological and cardiovascular disorders.

Enterovirus consists of a simple virus capsid and a single strand of positive sense RNA. The capsid contains four proteins, VP1 to VP4. Variations within capsid proteins VP1 to VP3 are responsible for antigenic diversity among enterovirus, with neutralization sites most densely clustered on VP1 (Rueckert, *Virology*, Lippincott-Raven, New York, 1990, 507). Replication of RNA viruses is directed by viral RNA polymerase of low fidelity, i.e., an error frequency of $10^{-3}$ to $10^{-4}$ misincorporated nucleotide per round of replication (Holland et al., *Science*, 1982, 215:1576–1585; Ward et al., *J. Virol.*, 1988, 62:558–562; and La Torre et al., *J. Virol.*, 1990, 64:664–671). In other words, replication of an enterovirus genome consisting of about 7500 nucleotides results in a population of genomes having on average at least one mutation. Moreover, recombination occurs at a very high frequency in the picornaviruse family (McCahon, *Arch. Virol.*, 1981, 69:1–23).

SUMMARY

One aspect of the present invention relates to a compound of formula I:

formula I

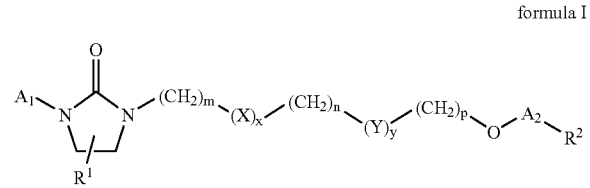

Forumula I wherein each of $R^1$ and $R^2$, independently, is H, halo, $C_{1-5}$ alkyl, $C_{1-5}$ haloalkyl, $C_{6-12}$ aryl, $C_{6-12}$ aralkyl, or heteroaryl, optionally substituted with halo, —$OR^a$, $C_{1-5}$ alkyl, substituted aryl, substituted heteroaryl, $C_{1-5}$ haloalkyl, $C_{1-5}$ alkyl-$OR^a$, —CN, —C(O)$R^a$, —$SR^a$, —S(O)$R^a$, —S(O)$_2R^a$, —$NR^aR^{a'}$, —C(O)$OR^a$, —C(O)$NR^aR^a$, —$NO_2$, —OC(O)$R^a$, —$NR^aC(O)R^{a'}$, —$NR^aC(O)OR^{a'}$, or —$NR^aC(O)NR^{a'}R^{a''}$; in which each of $R^a$, $R^{a'}$, and $R^{a''}$, independently, is H, $C_{1-5}$ alkyl, or aryl; each of $A_1$ and $A_2$, independently, is $C_{6-12}$ aryl, $C_{6-12}$ aralkyl, or heteroaryl, optionally substituted with halo, —$OR^b$, $C_{1-5}$ alkyl, $C_{1-5}$ haloalkyl, $C_{1-5}$ alkyl-$OR^b$, —CN, —$NO_2$, —C(O)$R^b$, —$SR^b$, —S(O)$R^b$, —S(O)$_2R^b$, —$NR^bR^{b'}$, —C(O)$OR^b$, —C(O)$NR^bR^{b'}$, —$NO_2$, —OC(O)$R^{b'}$, —$NR^bC(O)R^{b'}$, —$NR^bC(O)OR^{b'}$, or —$NR^bC(O)NR^{b'}R^{b''}$, provided that if $A_1$ is heteroaryl, it forms a C—N bond with the imidazolidinone ring; in which each of $R^b$, $R^{b'}$, and $R^{b''}$, independently, is H, $C_{1-5}$ alkyl, or aryl; each of X and Y, independently, is —C(H)($R^c$), —C($R^c$)($R^{c'}$)—, —$NR^{c''}$—, —S—, —S(O)—, —S(O)$_2$—, —C(H)(O$R^d$)—, —C(H)[OC(O)$R^d$]—, —C(H)(N$R^dR^{d'}$)—, —C(H)[N$R^dC(O)R^{d'}$]—, —C(H)[N$R^dC(O)OR^{d'}$], —C(H)[N$R^dC(O)NR^{d'}R^{d''}$], —C(H)(SH)—, —C(H)(S$R^d$)—, —C(H)(SO$R^d$)—, —C(H)(SO$_2R^d$)—, $C_{6-12}$ aryl, cyclyl, heterocyclyl, heteroaryl, alkenyl, alkynyl,

or

;

in which each of $R^c$ and $R^{c'}$, independently, is halo, $C_{1-5}$ alkyl, $C_{1-5}$ haloalkyl, $C_{1-5}$ hydroxyalkyl, $C_{1-5}$ aminoalkyl, $C_{6-12}$ aryl, $C_{6-12}$ aralkyl, or heteroaryl; $R^{c''}$ is $C_{1-5}$ alkyl, $C_{1-5}$ haloalkyl, $C_{1-5}$ hydroxyalkyl, $C_{1-5}$ aminoalkyl, $C_{6-12}$ aryl, $C_{6-12}$ aralkyl, or heteroaryl; and each of $R^d$, $R^{d'}$, and $R^{d''}$, independently, is H, $C_{1-5}$ alkyl, or aryl; each of m, n, and p, independently, is 0, 1, 2, 3, 4, or 5; and each of x and y, independently, is 0 or 1, provided that at least one of x and y is 1.

Referring to formula I above, one subset of the compounds are featured by that x is 1, y is 0, and p is 0. In some instances, $R^1$ is H and $A_1$ is pyridyl. In these compounds, $A_2$ can be phenyl and $R^2$ can be H, halo, $C_{1-5}$ alkyl, $C_{1-5}$ haloalkyl, $C_{6-12}$ aryl, $C_{6-12}$ aralkyl, or heteroaryl, optionally substituted with halo, —$OR^a$, $C_{1-5}$ alkyl, substituted aryl, substituted heteroaryl, $C_{1-5}$ haloalkyl, substituted aryl, substituted heteroaryl, $C_{1-5}$ alkyl-$OR^a$, —CN, —C(O)$R^a$, —$SR^a$, —S(O)$R^a$, —S(O)$_2R^a$, —$NR^aR^{a'}$, —C(O)$OR^a$, —C(O)$NR^aR^{a'}$, —$NO_2$, —OC(O)$R^a$, —$NR^aC(O)R^{a'}$, —$NR^aC(O)OR^{a'}$, or —$NR^aC(O)NR^{a'}R^{a''}$; in which each of $R^a$, $R^{a'}$, and $R^{a''}$, independently, is H, or $C_{1-5}$ alkyl, or aryl.

Another subset of the compounds are featured by that $R^1$ is H. In some instances, $A_1$ is pyridyl. In these compounds, $A_2$ can be phenyl, and $R^2$ can be phenyl or heteroaryl substituted with halo, —$OR^a$, $C_{1-5}$ alkyl, substituted aryl, substituted heteroaryl, $C_{1-5}$ haloalkyl, $C_{1-5}$ alkyl-$OR^a$, —CN, —C(O)$R^a$, —$SR^a$, —S(O)$R^a$, —S(O)$_2R^a$, —$NR^aR^{a'}$, —C(O)$OR^a$, —C(O)$NR^aR^{a'}$, —$NO_2$, —OC(O)$R^a$, —$NR^aC(O)R^{a'}$, —$NR^aC(O)OR^{a'}$, or —$NR^aC(O)NR^{a'}R^{a''}$; in which each of $R^a$, $R^{a'}$, and $R^{a''}$, independently, is H, $C_{1-5}$ alkyl, or aryl.

Shown below are exemplary compounds of this invention:

Compound 1

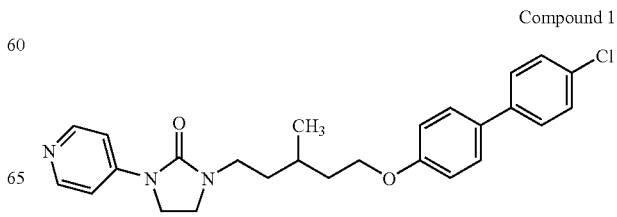

-continued
Compound 2
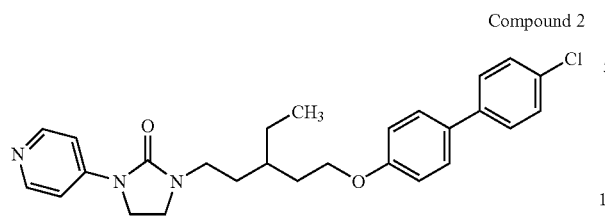
Compound 3
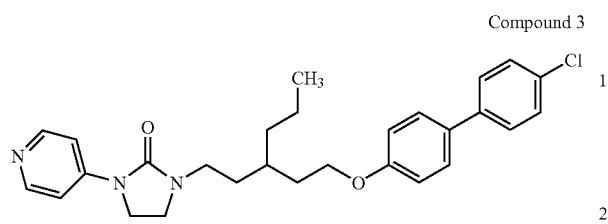
Compound 4
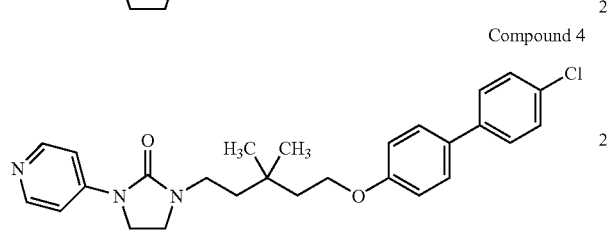
Compound 5
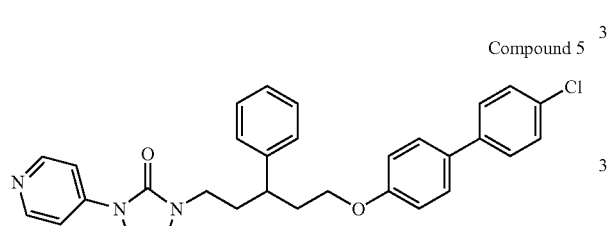
Compound 6
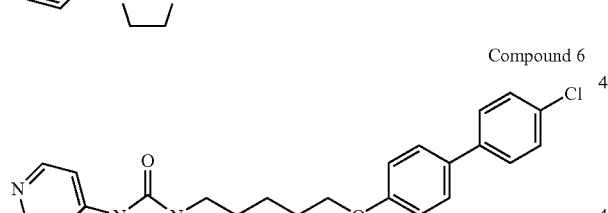
Compound 7
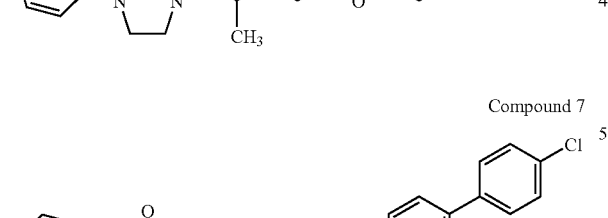
Compound 8
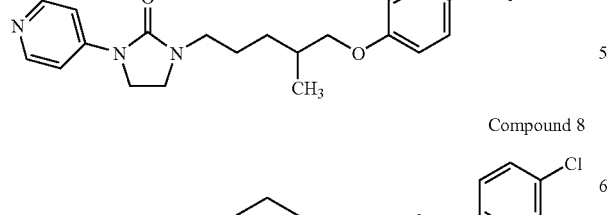
-continued
Compound 9
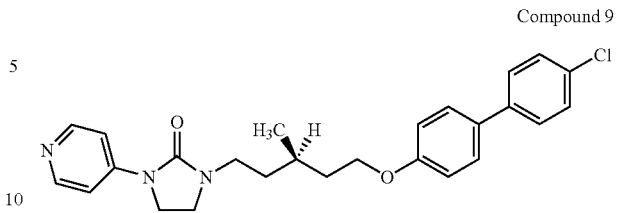
Compound 10
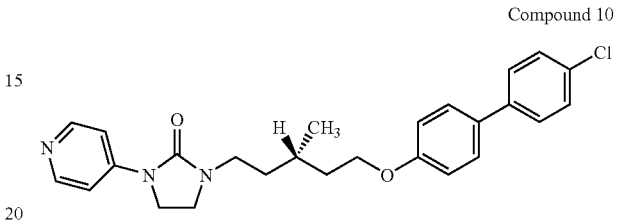
Compound 11
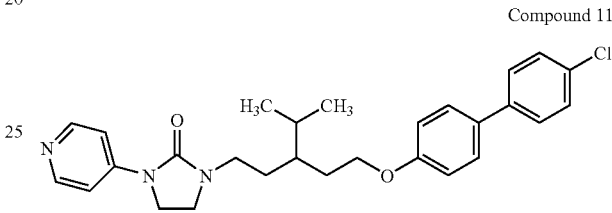
Compound 12
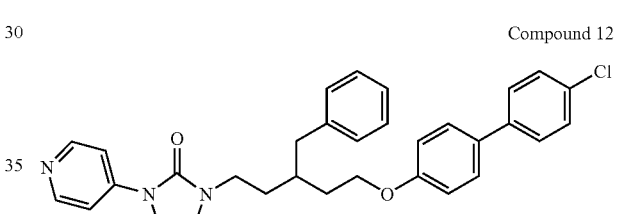
Compound 13
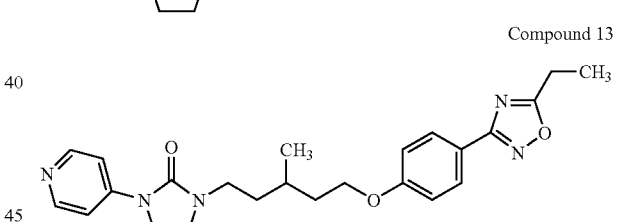
Compound 14
Compound 15
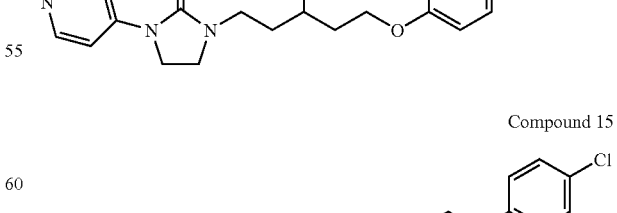

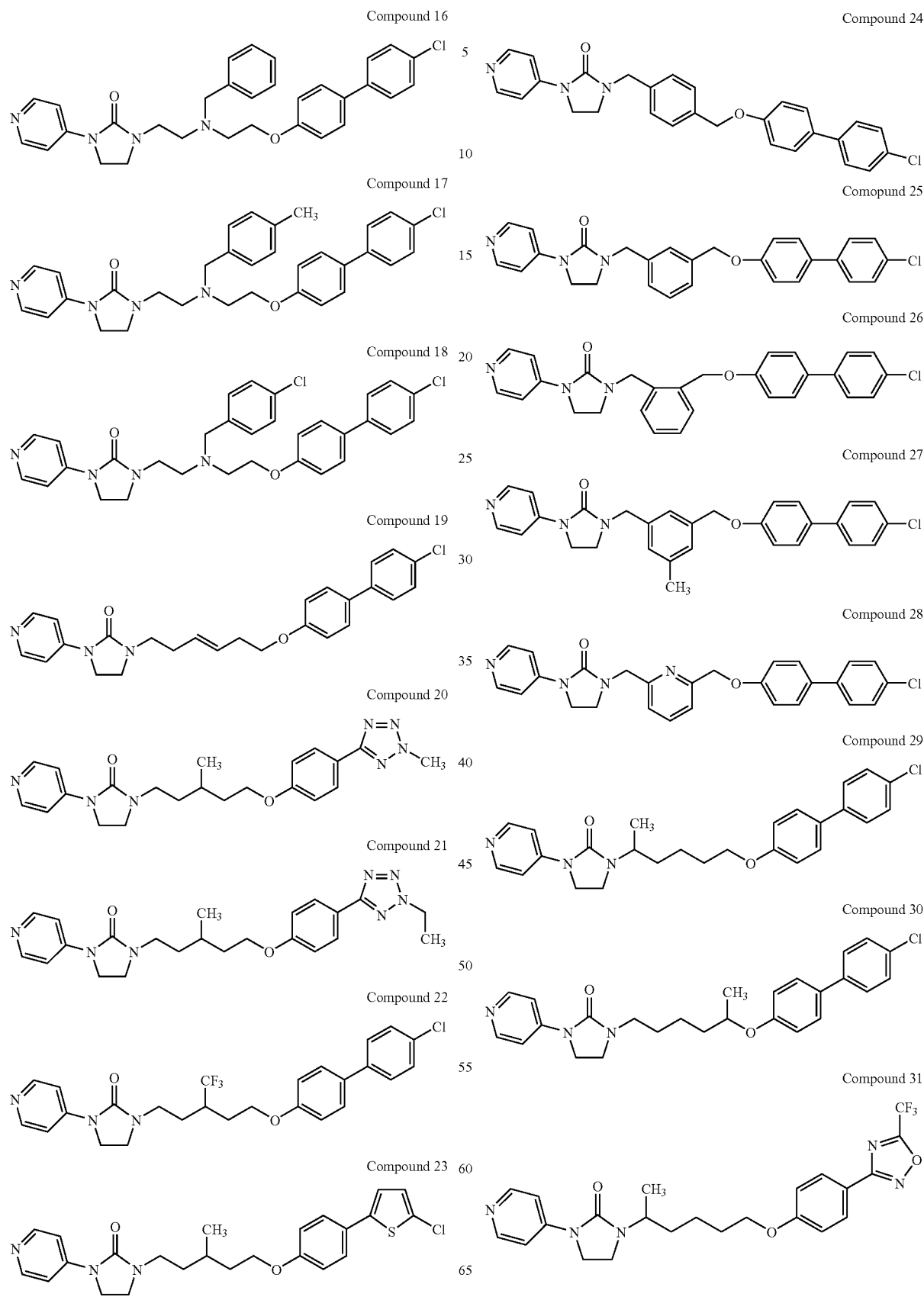

Compound 32
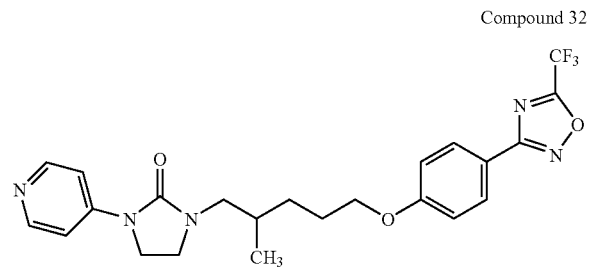
Compound 33
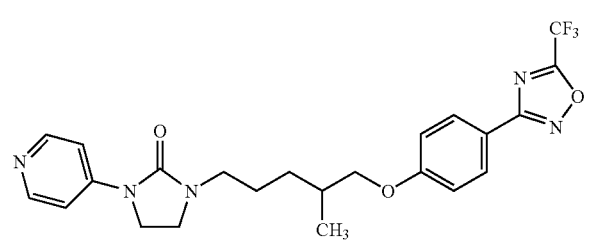
Compound 34
Compound 35
Compound 36
Compound 37
Compound 38
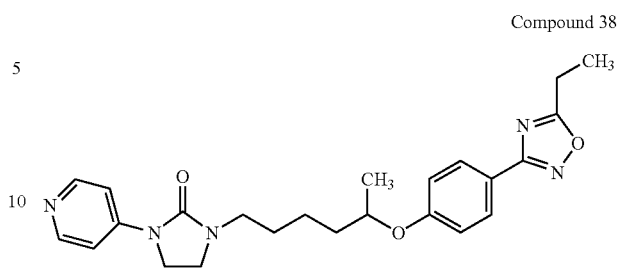
Compound 39
Compound 40
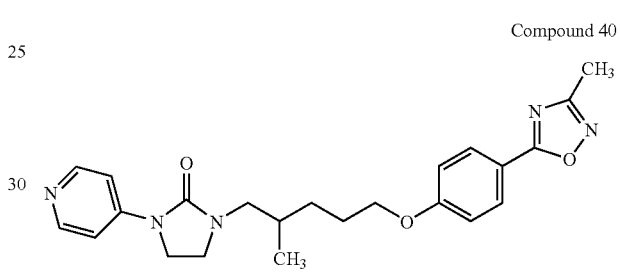
Compound 41
Compound 42
Compound 43

-continued

Compound 44
Compound 45
Compound 46
Compound 47
Compound 48
Compound 49
Compound 50

-continued

Compound 51
Compound 52
Compound 53
Compound 54
Compound 55
Compound 56
Compound 57
Compound 58

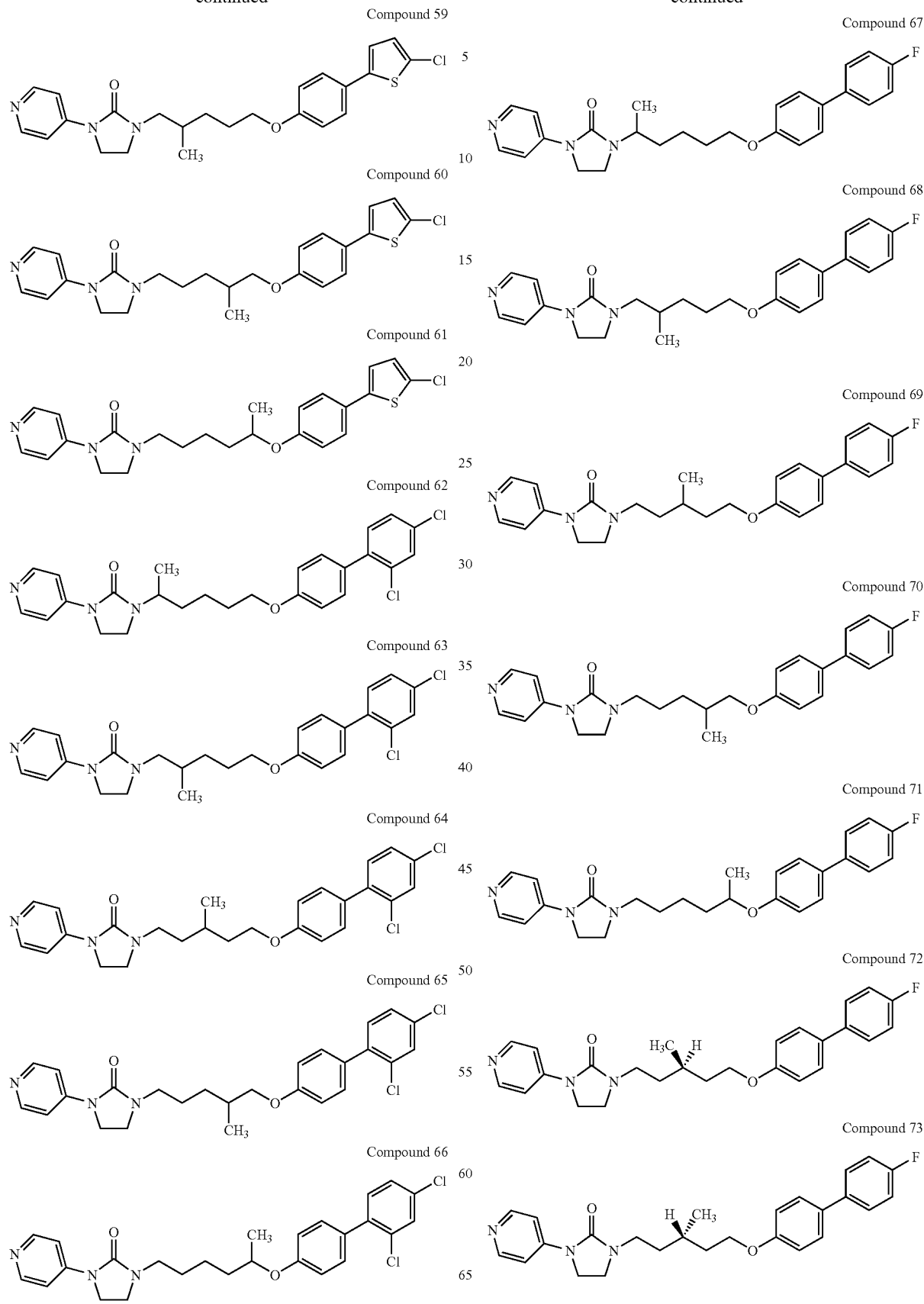

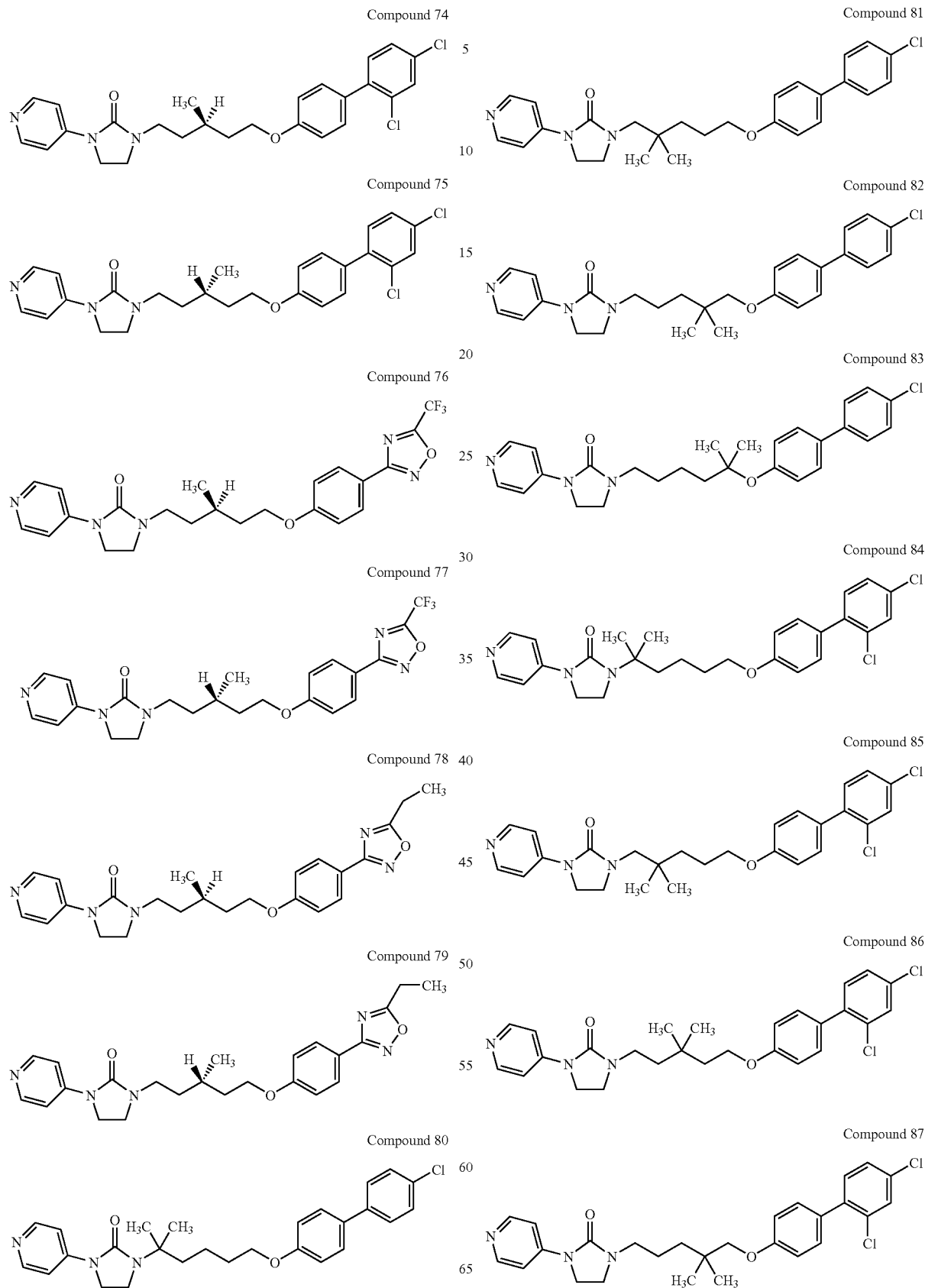

Compound 88
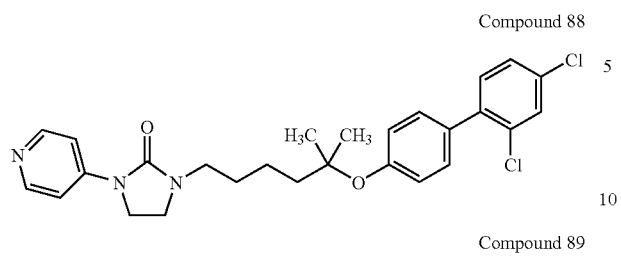
Compound 89
Compound 90
Compound 91
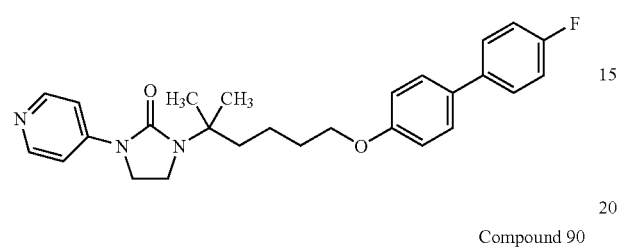
Compound 92
Compound 93
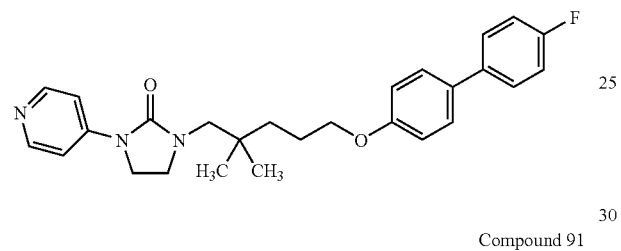
Compound 94
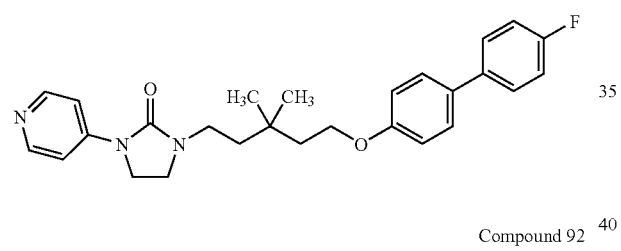
Compound 95
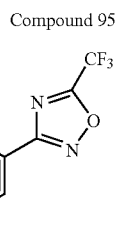
Compound 96
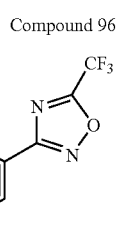
Compound 97
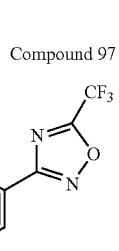
Compound 98
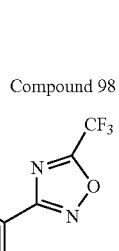
Compound 99
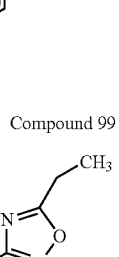
Compound 100
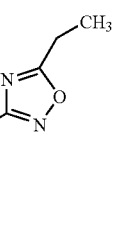

-continued

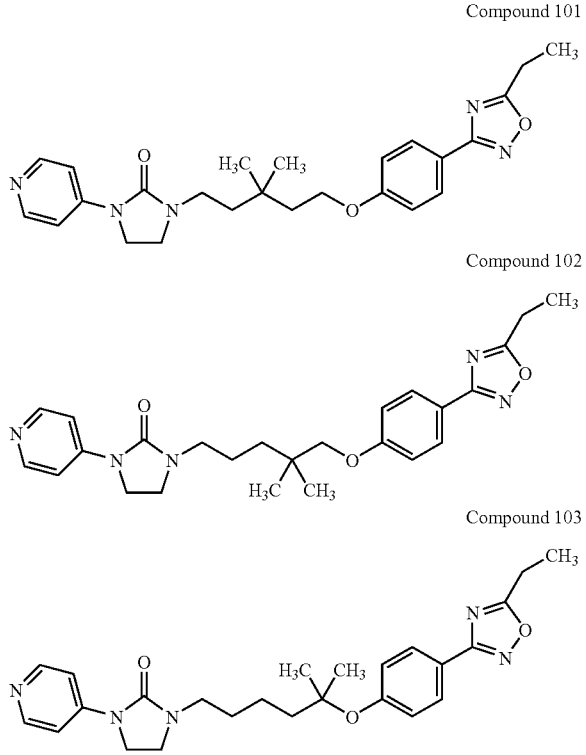

Compound 101

Compound 102

Compound 103

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$–$C_{10}$ alkyl refers to an alkyl group that contains 1 to 10 (inclusive) carbon atoms. The term "alkoxy" refers to an —O-alkyl radical. The term "aminoalkyl" refers to an alkyl group substituted with one or more amino groups. The term "haloalkyl" refers to an alkyl group substituted with one or more halo radicals. The term "hydroxyalkyl" refers to alkyl substituted with one or more hydroxy groups.

The term "alkenyl" refers to a hydrocarbon chain that may be a straight chain or branched chain having one or more carbon-carbon double bonds. The term "alkynyl" refers to a hydrocarbon chain that may be a straight chain or branched chain having one or more carbon-carbon triple bonds.

The term "aryl" refers to a 6-carbon monocyclic or 10-carbon bicyclic aromatic ring system wherein each ring may have 1 to 4 substituents. Examples of aryl groups include phenyl, naphthyl and the like. The term "aryloxy" refers to an —O-aryl radical. The term "aralkyl" refers to alkyl substituted with an aryl.

The term "cyclyl" refers to a saturated and partially unsaturated cyclic hydrocarbon group having 3 to 12 carbons, preferably 3 to 8 carbons, and more preferably 3 to 6 carbons, wherein the cyclyl group may be optionally substituted. Examples of cyclyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5–8 membered monocyclic, 8–12 membered bicyclic, or 11–14 membered tricyclic ring system having 1–3 heteroatoms if monocyclic, 1–6 heteroatoms if bicyclic, or 1–9 heteroatoms if tricyclic, said heteroatoms selected from O, N, or S (e.g., carbon atoms and 1–3, 1–6, or 1–9 heteroatoms of N, O, or S if monocyclic, bicyclic, or tricyclic, respectively), wherein each ring may have 1 to 4 substituents. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5–8 membered monocyclic, 8–12 membered bicyclic, or 11–14 membered tricyclic ring system having 1–3 heteroatoms if monocyclic, 1–6 heteroatoms if bicyclic, or 1–9 heteroatoms if tricyclic, said heteroatoms selected from O, N, or S (e.g., carbon atoms and 1–3, 1–6, or 1–9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, carbonyl, carbamido, carbamyl, carboxyl, thioureido, thiocyanato, sulfoamido, alkyl, alkenyl, alkyloxy, aryl, heteroaryl, cyclyl, heterocyclyl, wherein alkyl, alkenyl, alkyloxy, aryl, heteroaryl cyclyl, and heterocyclyl are optionally substituted with alkyl, aryl, heteroaryl, halogen, hydroxyl, amino, mercapto, cyano, or nitro.

The compounds described above include their pharmaceutically acceptable salts and prodrugs, if applicable. Such a salt can be formed between a negatively charged ionic group in an imidazolidinone compound (e.g., carbonate) and a positively charged counterion (e.g., sodium, potassium, calcium, or magnesium). Likewise, a positively charged ionic group in an imidazolidinone compound (e.g., ammonium) can also form a salt with a negatively charged counterion (e.g., chloride, bromide, or iodide). Examples of such imidazolidinone salts include the hydrochloride salt of 1-[5-(4'-chloro-biphenyl-4-yloxy)-3-methyl-pentyl]-3-pyridin-4-yl-imidazolidin-2-one. Examples of prodrugs include esters and other pharmaceutically acceptable compounds, which, upon administration to a subject, are capable of providing imidazolidinone compounds described above.

The compounds of this invention can be used as antiviral agents, particularly against human enterovirus. Accordingly, another aspect of this invention relates to an imidazolidinone compound as an agent against infection by enterovirus; a method of treating infection by enterovirus, i.e., administering to a subject in need thereof an effective amount of one of the imidazolidinone compounds; and a method of using such an imidazolidinone compound to manufacture a medicament used in treating infection by enterovirus. The invention also relates to a composition containing one of the imidazolidinone compounds described above and a pharmaceutically acceptable carrier.

The details of many embodiments of the invention are set forth in the description below. Other features, objects, and advantages of the invention will be apparent from the description and the claims.

DETAILED DESCRIPTION

The imidazolidinone compounds of this invention can be synthesized by one of methods (I)–(IX) described below. Also shown below are Schemes 1–10, which illustrate these methods. In the schemes, $R^1$, $R^2$, $A_1$, $A_2$, X, Y, m, n, and p are as defined above; and each of $R^{10}$, $R^{11}$, and $R^{12}$, independently, is H, halo, $C_{1-5}$ alkyl, aryl, heteroaryl, cyclyl, heterocyclyl, and $C_{1-5}$ alkyl haloalkyl.

Method (I): Method (I) is shown in Scheme 1. 4-Aminopyridine is coupled with 2-chloroethylisocyanate to give a N-(2-chloroethyl)urea compound. Subsequent intramolecular cyclization of the N-(2-chloroethyl)urea compound in the presence of sodium hydride results in the formation of cyclic urea A in a quantitative yield (Otto Meth-Cohn et al., *J. Chem. Soc., Perkin Trans.* 1 1998, 423–436). The cyclic urea A is reacted with compound D, an alkylating agent, to afford imidazolidinone compound E. Compound D is synthesized from compound B and commercially available substituted phenol C. Alternatively, compound D can be synthesized via a two-step procedure using Suzuki coupling as a key operation as shown in Scheme 2 (Kabalka, G. W. et al., *J. Chem. Soc., Chem. Commun.* 2001, 775; Dyer, U. C. et al., *Tetrahedron Lett.* 2001, 42, 1765–1767). See Scheme 2.

Scheme 1

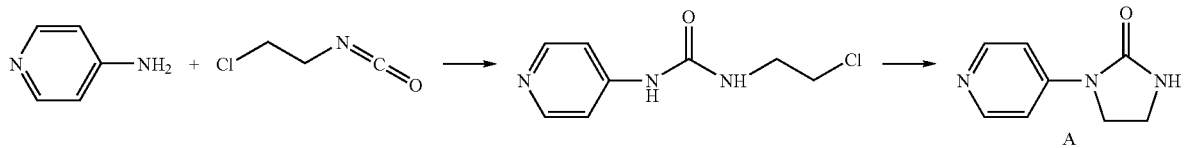

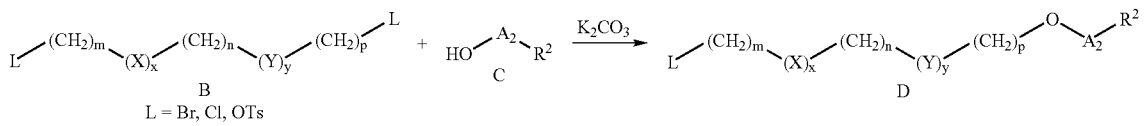

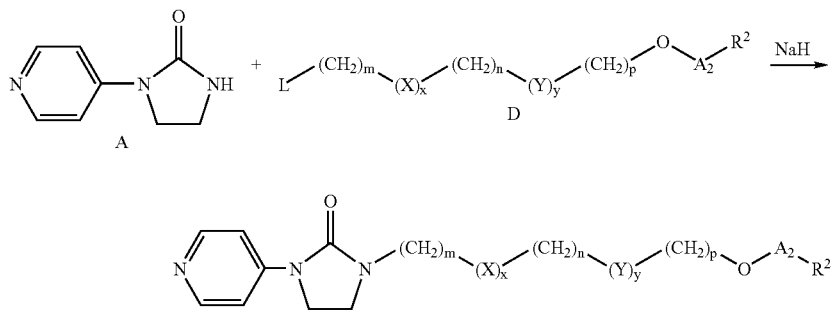

Scheme 2

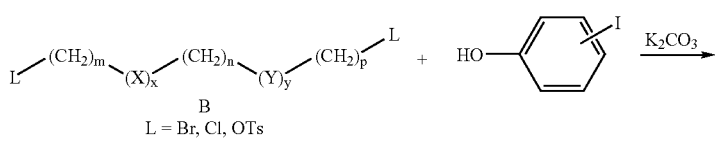

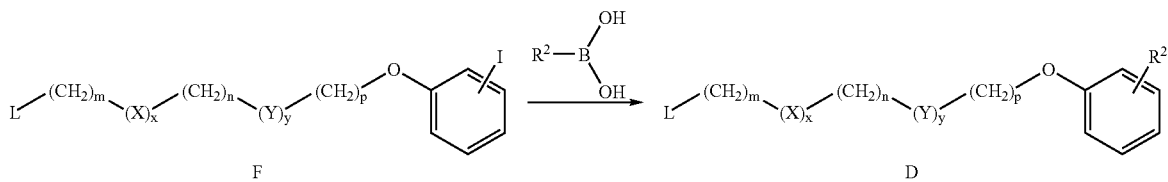

Method (II): Method (II) is shown in Scheme 3. Compound A is treated with an electrophile B in the presence of sodium hydride to give an intermediate, compound G. Treatment of compound G with 2,4,6-trisubstituted phenol C and potassium carbonate affords the desired compound E.

Scheme 3

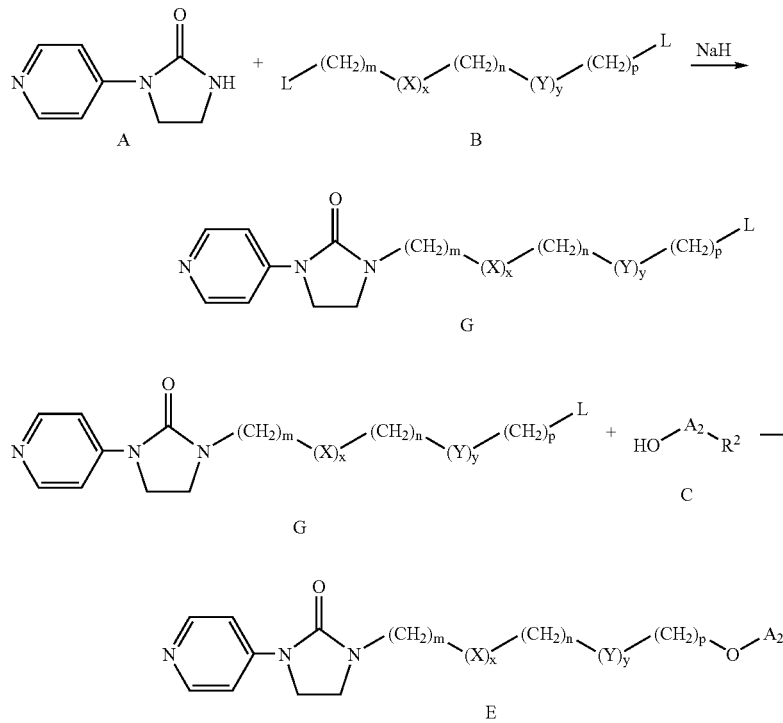

Method (III): Scheme 4 shows synthesis of a compound of formula I, in which $R^2$ is 1,2,4-oxadiazole. (Guy D. Diana et al., *J. Med. Chem.* 1994, 37: 2421–2436): Compound A is reacted with benzonitrile H to form an intermediate I. Treatment of the intermediate with hydroxylamine hydrochloride and potassium carbonate affords the corresponding amidoxime which is acylated with the appropriate acid chloride to give compound J.

Scheme 4

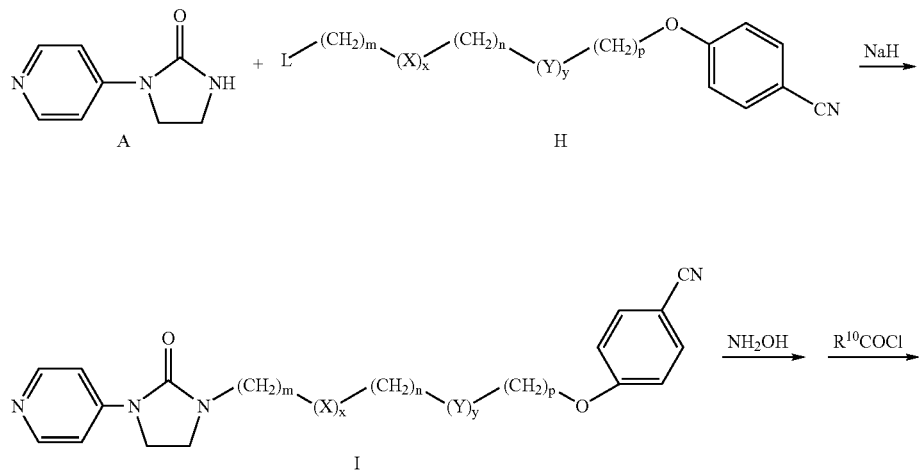

-continued

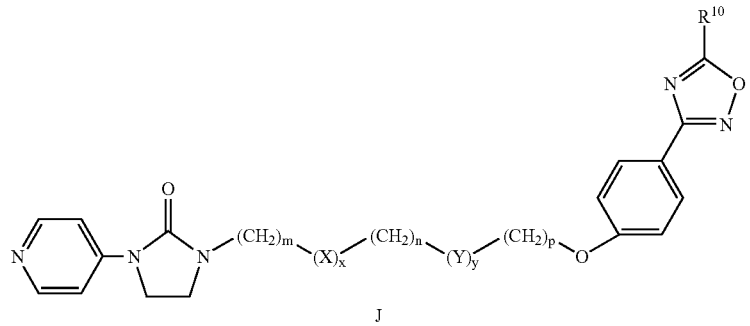

J

Method (IV): Scheme 5 shows synthesis of a compound of formula I, in which $R^2$ is 1,2,4-oxadiazol-5-yl. Hydrolysis of benzonitrile I gives a high yield of an amide intermediate. The intermediate is reacted with dimethylacetamide dimethyl acetal to give acylamidine. The acylamidine compound then is treated with hydroxylamine to afford compound K in a moderate to high yield.

Scheme 5

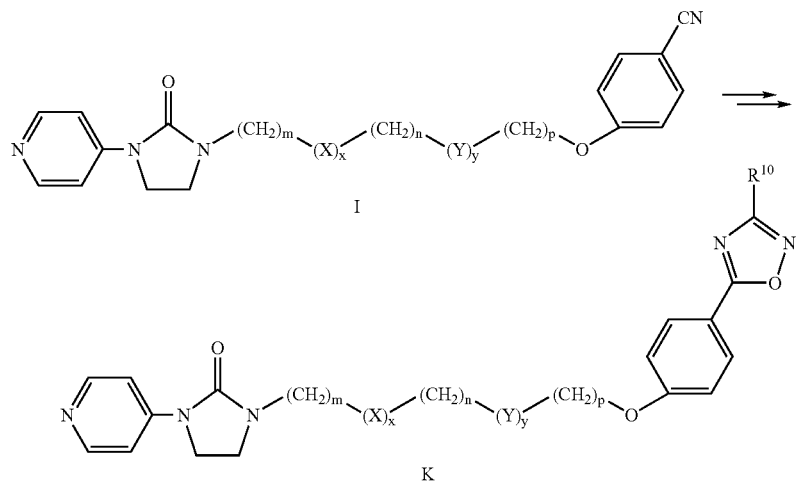

Method (V): Scheme 6 shows synthesis of a compound of formula I, in which $R^2$ is 1,3,4-oxadiazolyl (Guy D. Diana et al., *J. Med. Chem.* 1994, 37: 2421–2436). The desired compound M is obtained by cyclization of a diacylhydrazine compound, which is synthesized from compound L.

Scheme 6

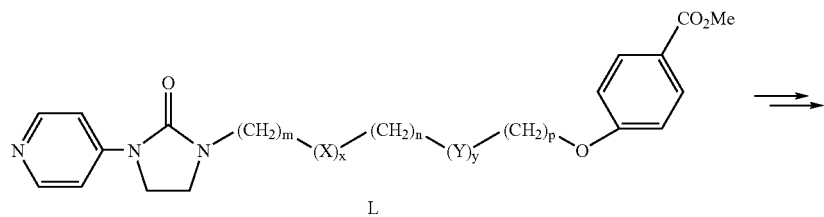

L

-continued

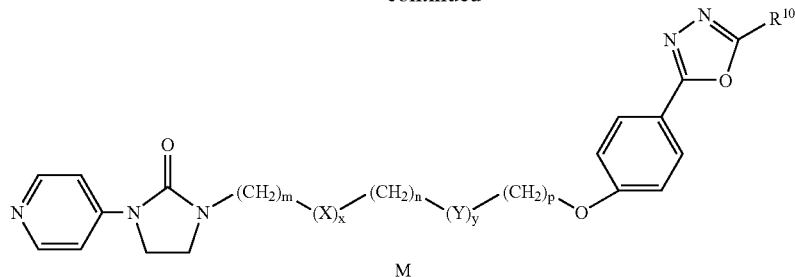

M

Method (VI): Scheme 7 shows synthesis of a compound of formula I, in which $R^2$ is unsubstituted tetrazole (Guy D. Diana et al., *J. Med. Chem.* 1993, 36: 3240–3250). Treatment of compound I with sodium azide and ammonium chloride gave non-substituted tetrazole N.

Scheme 7

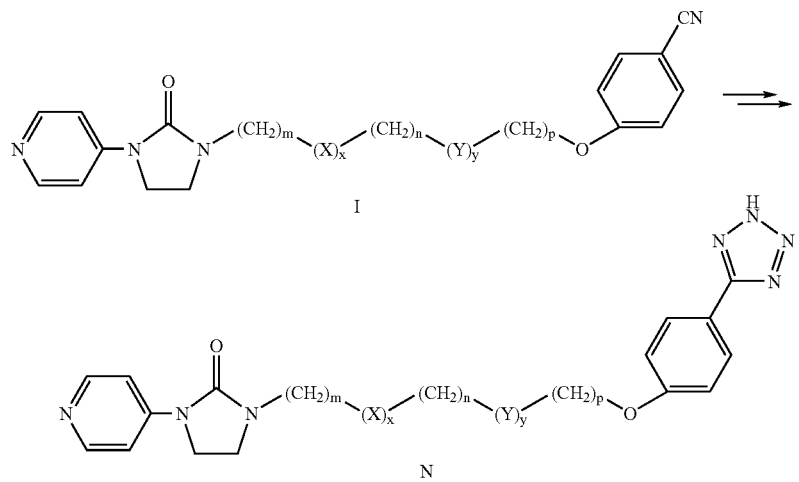

Method (VII): Scheme 8 shows synthesis of a compound of formula I, in which $R^2$ is substituted tetrazole (Guy D. Diana et al., *J. Med. Chem.* 1993, 36, 3240–3250). 1-Substituted tetrazole O, is prepared in four steps from 4-hydroxy-3,5-disubstituted-benzonitrile. Nucleophilic substitution of 1-substituted tetrazole O with compound B provides an intermediate. The intermediate is treated with compound A in the presence of sodium hydride in N,N-dimethylformamide to afford the desired compound P.

Scheme 8

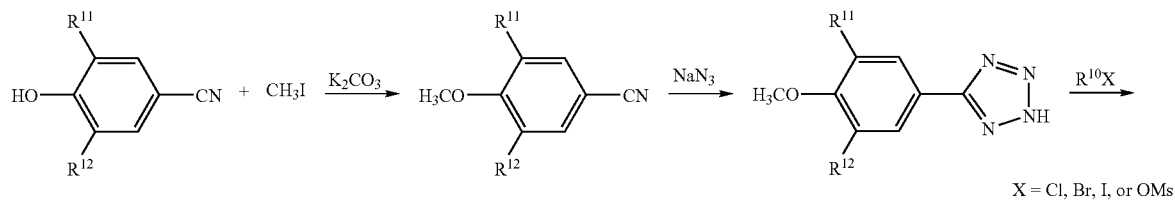

X = Cl, Br, I, or OMs

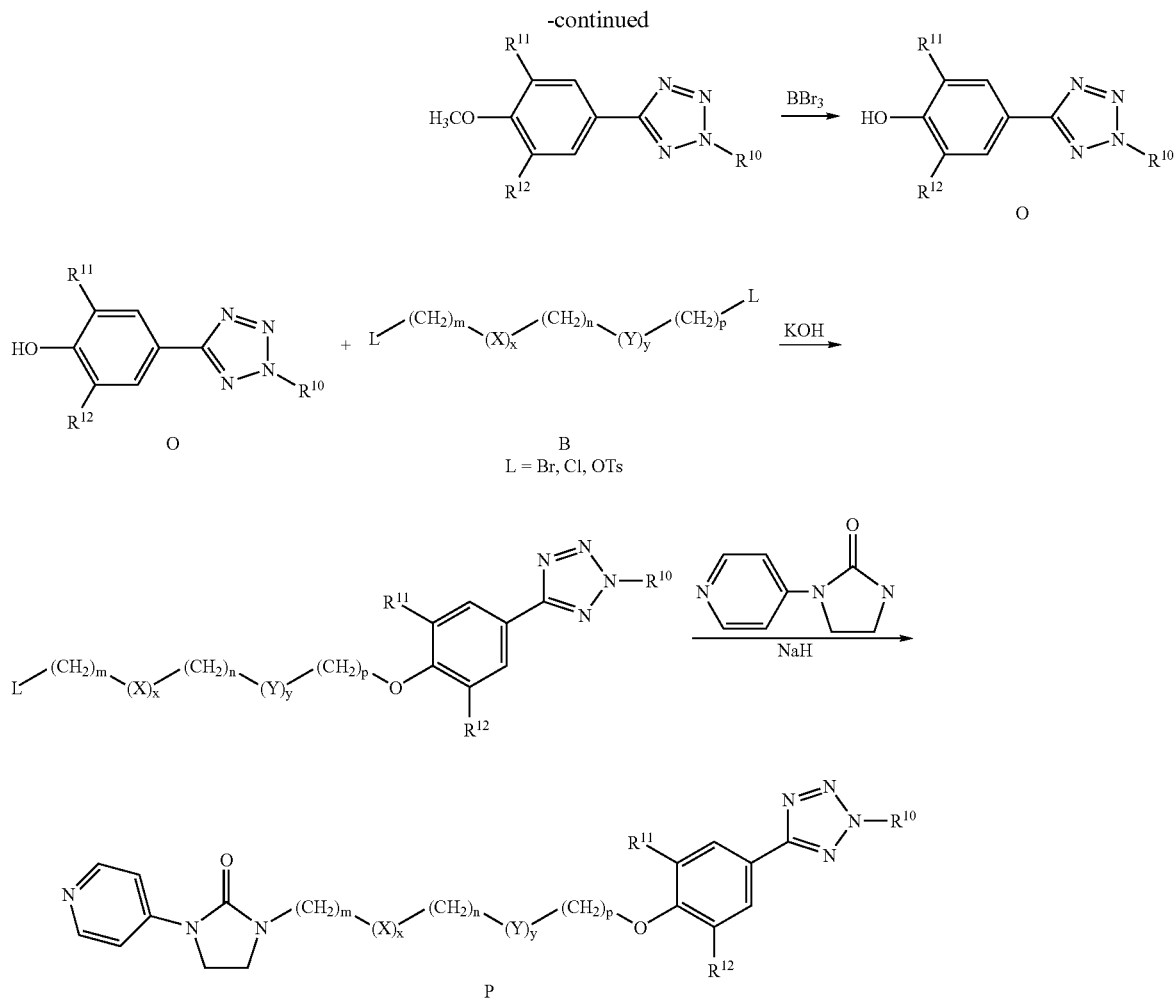

Methods (VIII) and (IX): Schemes 9 and 10 show synthesis of enantiomerically pure methyl (R)-(+)-3-methylglutarate and methyl (S)-(−)-3-methylglutarate, respectively. (±)-Methyl hydrogen 3-methylglutarate, (R)-$X_1$ and (S)-$X_1$, are prepared from 3-methylglutaric acid according to the literature (Narendra Nath Saha et al., *J. Am. Chem. Soc.* 1959, 81: 3670–3674), and are resolved by crystallization of the corresponding diastereomeric cinchonidine salts from water (Renzo Rossi et al., *Tetrahedron* 1985, 41: 627–633; J. Bryan Jones et al., *J. Chem. Soc., Chem. Commun.* 1984: 579–580). After six crystallizations, the salts are treated with diluted HCl to give the resolved acid (R)-$X_1$, ([α]+0.58 (neat)). The mother liquors are concentrated, acidified and extracted with ether to afford (S)-$X_1$ ([α]−0.18 (neat)).

In Method (VIII), (R)-$X_1$ is reduced with borane-tetrahydrofuran complex and the resulting hydroxyester (R)-$X_2$ is further converted to a tosylate compound (R)-$X_3$. Then (R)-$X_3$ is reacted with substituted phenol $X_4$ in the presence of potassium carbonate to afford an ester (R)-$X_5$. Reduction of the ester (R)-$X_5$ with lithium aluminum hydride gives an alcohol compound (R)-$X_6$. The alcohol compound (R)-$X_6$ is transformed into its tosylate form (R)-$X_7$. (R)-$X_7$ is then reacted with the compound A in the presence of sodium hydride to afford the desired compound (S)-$X_8$.

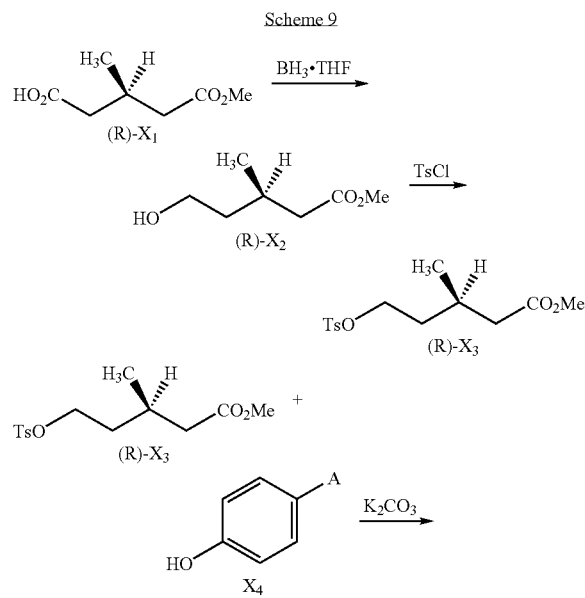

Scheme 9

In Method (IX), (S)-$X_1$ is reduced with borane-tetrahydrofuran complex and the resulting hydroxyester (S)-$X_2$ is converted into the corresponding tosylate (S)-$X_3$. Then (S)-$X_3$ is reacted with substituted phenol $X_4$ in the presence of potassium carbonate to afford (S)-$X_5$. Reduction of the ester (R)-$X_5$ with lithium aluminum hydride gives an alcohol compound (S)-$X_6$. The alcohol compound (S)-$X_6$ is transformed into its tosylate form (S)-$X_7$. (S)-$X_7$ is then reacted with the compound A, in the presence of sodium hydride to afford the desired compound (R)-$X_8$.

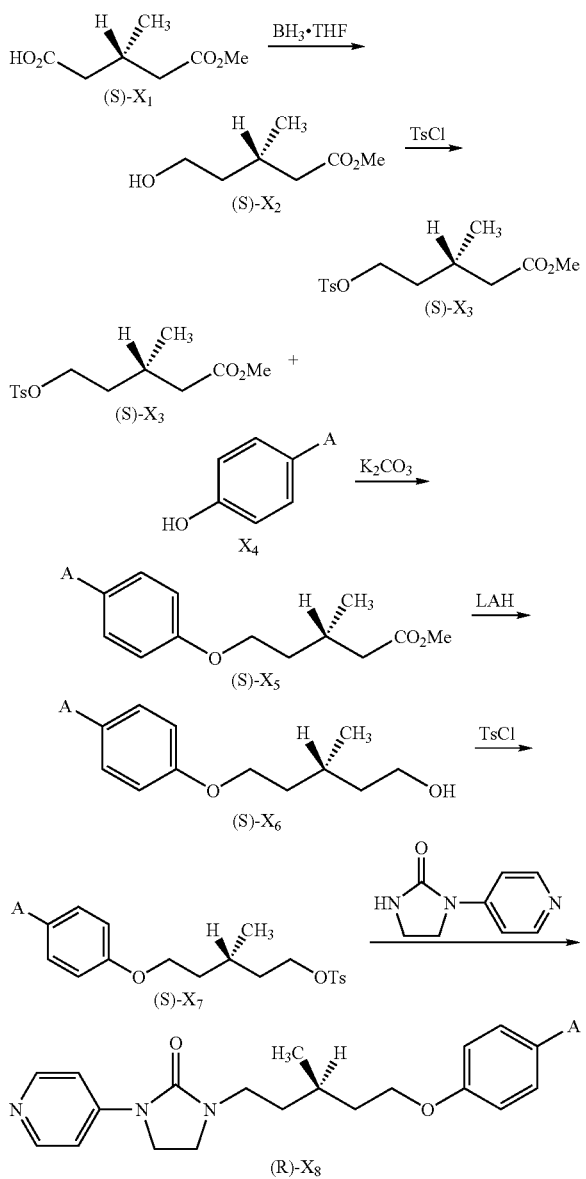

The imidazolidinone compounds of this invention may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition contains an effective amount of at least one of the imidazolidinone compounds described above and a pharmaceutical acceptable carrier. Further, this invention covers a method of administering an effective amount of one or more imidazolidinone compounds to a patient infected by enterovirus. "An effective amount" refers to the amount of the compound which is required to confer therapeutic effect on the treated subject. The effective amount varies, as recognized by those skilled in the art, depending on the types of diseases treated, route of administration, excipient usage, and the possibility of co-usage with other therapeutic treatment.

To practice the method of the present invention, a composition having one or more imidazolidinone compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active imidazolidinone compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active aminoquinoline compound. Examples of other carriers include colloidal silicon oxide, magnesium stearate, cellulose, sodium lauryl sulfate, and D&C Yellow # 10.

The imidazolidinone compounds of this invention can be preliminarily screened by an in vitro inhibition assay (e.g., plaque reduction assay) for their activity against viruses, and particularly, enterovirus. Compounds that demonstrates high activity in the preliminary screening can be further evaluated by in vivo methods well known in the art (see, e.g., Daniel C. Pevear et al., *Antimicrobial Agents & Chemotherapy*, 1999, 43(9): 2109–2115).

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Synthesis of Compound 1 (Method (I))

1-[5-(4'-Chloro-biphenyl-4-yloxy)-3-methyl-pentyl]-3-pyridin-4-yl-imidazolidin-2-one

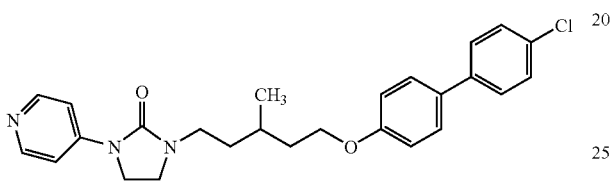

A suspension of 1-(4-pyridyl)-2-imidazolidinone (0.10 g, 0.61 mmol) and sodium hydride (75% dispersion in mineral oil, 0.02 g, 0.67 mmol) in anhydrous DMF (7 mL) was cooled in an ice bath and stirred at 0° C. for 30 minutes, followed by addition of a solution of 4-(5-bromo-3-methyl-pentyloxy)-4'-chloro-biphenyl (0.22 g, 0.61 mmol) in anhydrous DMF (5 mL). After 5 minutes, the ice bath was removed and the reaction mixture was stirred at room temperature for 6 hours. The reaction was quenched with water followed by extraction with ethyl acetate (100 mL×3). The organic layers were combined and washed with brine, dried over magnesium sulfate, and concentrated under reduced pressure. The crude mixture thus obtained was purified with flash column chromatography [dichloromethane/methanol (10:1)] to yield Compound 1 as a white solid (0.19 g, 71%).

$^1$H NMR (CDCl$_3$), δ (ppm): 8.41 (d, J=5.7 Hz, 2H), 7.43–7.46 (m, 6H), 7.34–7.36 (m, 2H), 6.92 (d, J=8.4 Hz, 2H), 4.01–4.06 (m, 2H), 3.75–3.80 (m, 2H), 3.48–3.55 (m, 2H), 3.34–3.42 (m, 2H), 1.75–1.90 (m, 2H), 1.69–1.73 (m, 2H), 1.44–1.48 (m, 1H), 1.03–1.05 (d, J=6.6 Hz, 3H). MS (EI): m/z 450 (M+H).

EXAMPLE 2

Synthesis of Compound 2 (Method (I))

1-[5-(4'-Chloro-biphenyl-4-yloxy)-3-ethyl-pentyl]-3-pyridin-4-yl-imidazolidin-2-one

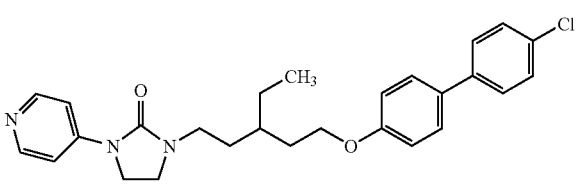

A suspension of 1-(4-pyridyl)-2-imidazolidinone (0.10 g, 0.61 mmol) and sodium hydride (75% dispersion in mineral oil, 0.02 g, 0.67 mmol) in anhydrous DMF (7 mL) was cooled in an ice bath and stirred at 0° C. for 30 minutes, followed by addition of a solution of toluene-4-sulfonic acid 5-(4'-chloro-biphenyl-4-yloxy)-3-ethyl-pentyl ester (0.29 g, 0.61 mmol) in anhydrous DMF (5 mL). After 5 minutes, the ice bath was removed and the reaction mixture was stirred at room temperature for 6 hours. The reaction was quenched with water followed by extraction with ethyl acetate (100 mL×3). The organic layers were combined and washed with brine, dried over magnesium sulfate, and concentrated under reduced pressure. The crude mixture thus obtained was purified with flash column chromatography [a mixture of dichloromethane and methanol (10:1)] to yield Compound 2 as a white solid (0.21 g, 75%).

$^1$H NMR (CDCl$_3$), δ (ppm): 8.41 (d, J=4.8 Hz, 2H), 7.42–7.45 (m, 6H), 7.34–7.36 (m, 2H), 6.93 (d, J=8.7 Hz, 2H), 4.03 (t, J=6.5 Hz, 2H), 3.74–3.79 (m, 2H), 3.49–3.55 (m, 2H), 3.36 (t, J=7.2 Hz, 2H), 1.81–1.84 (m, 2H), 1.59–1.65 (m, 3H), 1.44–1.48 (m, 2H), 0.93 (t, J=7.4 Hz, 3H). MS (EI): m/z 464 (M+H).

EXAMPLE 3

Synthesis of Compound 3 (Method (I))

1-{3-[2-(4'-Chloro-biphenyl-4-yloxy)-ethyl]-hexyl}-3-pyridin-4-yl-imidazolidin-2-one

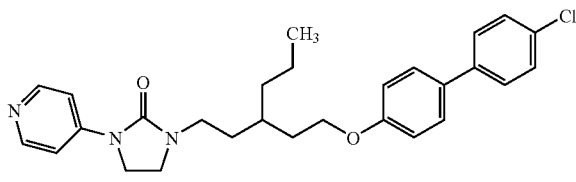

Compound 3 was prepared in a similar manner as described in Example 2.

$^1$H NMR (CDCl$_3$), δ (ppm): 8.41 (dd, J=5.1, 1.8 Hz, 2H), 7.42–7.45 (m, 6H), 7.34–7.37 (m, 2H), 6.91–6.94 (d, J=8.7 Hz, 2H), 4.03 (t, J=6.5 Hz, 2H), 3.73–3.78 (m, 2H), 3.49–3.54 (m, 2H), 3.36 (t, J=7.4 Hz, 2H), 1.81–1.84 (m, 2H), 1.59–1.64 (m, 3H), 1.36–1.39 (m, 4H), 0.90–0.94 (m, 3H). MS (EI): m/z 478 (M+H).

EXAMPLE 4

Synthesis of Compound 4 (General Procedure (I))

1-[5-(4'-Chloro-biphenyl-4-yloxy)-3,3-dimethyl-pentyl]-3-pyridin-4-yl-imidazolidin-2-one

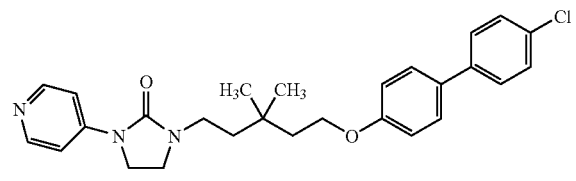

Compound 4 was prepared in a similar manner as described in Example 2.

$^1$H NMR (CDCl$_3$), δ (ppm): 8.42 (d, J=5.1 Hz, 2H), 7.44–7.46 (m, 6H), 7.34–7.37 (m, 2H), 6.94 (d, J=8.7 Hz, 2H), 4.07 (t, J=6.9 Hz, 2H), 3.77–3.82 (m, 2H), 3.51–3.56 (m, 2H), 3.35–3.41 (m, 2H), 1.81 (t, J=6.9 Hz, 2H), 1.55–1.60 (m, 2H), 1.06 (s, 6H). MS (EI): m/z 464 (M+H).

EXAMPLE 5

Synthesis of Compound 5 (Method (I))

1-[5-(4'-Chloro-biphenyl-4-yloxy)-3-phenyl-pentyl]-3-pyridin-4-yl-imidazolidin-2-one

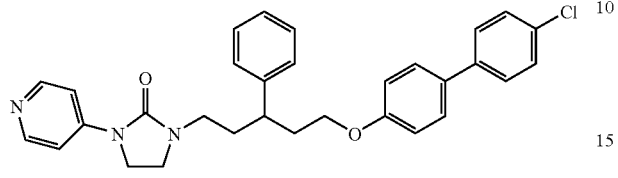

Compound 5 was prepared in a similar manner as described in Example 2.

$^1$H NMR (CDCl$_3$), δ (ppm): 8.41 (dd, J=5.0, 1.3 Hz, 2H), 7.32–7.91 (m, 7H), 7.17–7.28 (m, 6H), 6.83 (d, J=8.7 Hz, 2H), 3.69–3.87 (m, 2H), 3.51–3.67 (m, 2H), 3.31–3.48 (m, 2H), 3.19–3.29 (m, 2H), 2.88–3.0 (m, 1H), 2.17–2.28 (m, 2H), 1.95–2.08 (m, 2H). MS (EI): m/z 512 (M+H).

EXAMPLE 6

Synthesis of Compound 6 (Method (I))

1-[5-(4'-Chloro-biphenyl-4-yloxy)-2-methyl-pentyl]-3-pyridin-4-yl-imidazolidin-2-one

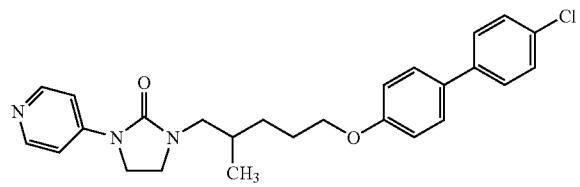

A suspension of 1-(4-pyridyl)-2-imidazolidinone (0.10 g, 0.61 mmol) and sodium hydride (75% dispersion in mineral oil, 0.02 g, 0.67 mmol) in anhydrous DMF (7 mL) was cooled in an ice bath and stirred at 0° C. for 30 minutes, followed by addition of a solution of toluene-4-sulfonic acid 5-(4'-chloro-biphenyl-4-yloxy)-2-methyl-pentyl ester (0.28 g, 0.61 mmol) in anhydrous DMF (5 mL). After 5 minutes, the ice bath was removed and the reaction mixture was stirred at room temperature for 6 hours. The reaction was quenched with water followed by extraction with ethyl acetate (100 mL×3). The organic layers were combined and washed with brine, dried over magnesium sulfate, and concentrated under reduced pressure. The crude mixture thus obtained was purified with flash column chromatography [a mixture of ethyl acetate and methanol (8:1)] to yield Compound 6 as a white solid (0.20 g, 73%).

$^1$H NMR (CDCl$_3$), δ (ppm): 8.42 (dd, J=4.9, 1.7 Hz, 2H), 7.41–7.47 (m, 6H), 7.32–7.37 (m, 2H), 6.92 (d, J=8.7 Hz, 2H), 3.98 (t, J=6.3 Hz, 2H), 3.55–3.81 (m, 2H), 3.49–3.53 (m, 2H), 3.11–3.23 (m, 2H), 1.77–1.99 (m, 3H), 1.57–1.64 (m, 1H), 1.30–1.33 (m, 1H), 0.98 (d, J=6.6 Hz, 3H). MS (EI): m/z 450 (M+H).

EXAMPLE 7

Synthesis of Compound 7 (Method (II))

1-[5-(4'-Chloro-biphenyl-4-yloxy)-4-methyl-pentyl]-3-pyridin-4-yl-imidazolidin-2-one

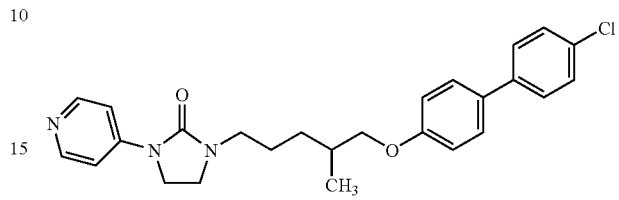

A suspension of toluene-4-sulfonic acid 2-methyl-5-(2-oxo-3-pyridin-4-yl-imidazolidin-1-yl)-pentyl ester (0.10 g, 0.24 mmol) and 4'-chloro-biphenyl-4-ol (0.05 g, 0.24 mmol) in anhydrous acetonitrile (30 mL) was stirred at room temperature for 10 minutes, followed by addition of potassium carbonate (0.07 g, 0.48 mmol). Then the reaction mixture was stirred at refluxed temperature for 12 hours. The reaction was quenched with a saturated aqueous ammonium chloride solution followed by extraction with ethyl acetate (100 mL×3). The organic layers were combined and washed with brine, dried over magnesium sulfate, and concentrated under reduced pressure. The crude mixture thus obtained was purified with flash column chromatography [a mixture of ethyl acetate and methanol (10:1)] to yield Compound 7 as a white solid (0.05 g, 50%).

$^1$H NMR (CDCl$_3$), δ (ppm): 8.42 (br, 2H), 7.43–7.45 (m, 6H), 7.34–7.36 (m, 2H), 6.91–6.94 (m, 2H), 3.77–3.82 (m, 4H), 3.50–3.56 (m, 2H), 3.31–3.35 (m, 2H), 1.99–2.01 (m, 2H), 1.56–1.70 (m, 2H), 1.25–1.31 (m, 1H), 1.05 (d, J=6.0 Hz, 3H). MS (EI): m/z 450 (M+H).

EXAMPLE 8

Synthesis of Compound 8 (Method (I))

1-(2-{1-[2-(4'-Chloro-biphenyl-4-yloxy)-ethyl]-cyclohexyl}-ethyl)-3-pyridin-4-yl-imidazolidin-2-one

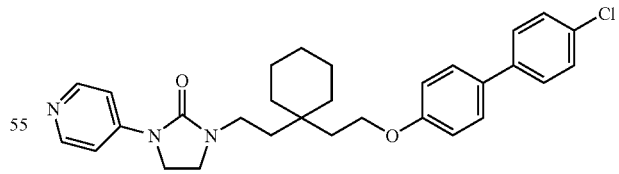

Compound 8 was prepared in a similar manner as described in Example 2.

$^1$H NMR (CDCl$_3$), δ (ppm): 8.42 (d, J=6.3 Hz, 2H), 7.43–7.46 (m, 6H), 7.34–7.37 (m, 2H), 6.95 (d, J=8.4 Hz, 2H), 4.08 (t, J=6.9 Hz, 2H), 3.75–3.81 (m, 2H), 3.51–3.57 (m, 2H), 3.34–3.39 (m, 2H), 1.88 (t, J=6.9 Hz, 2H), 1.61–1.66 (m, 2H), 1.24–1.49 (m, 10H). MS (EI): m/z 504 (M+H).

EXAMPLE 9

Synthesis of Compound 9 (Method (IX))

(R)-1-[5-(4'-Chloro-biphenyl-4-yloxy)-3-methyl-pentyl]-3-pyridin-4-yl-imidazolidin-2-one

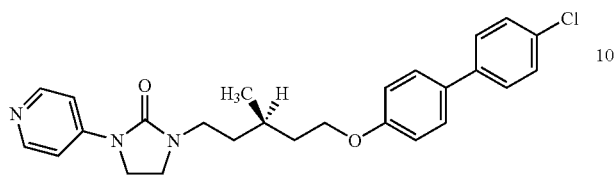

Compound 9 was prepared in a similar manner as described in Example 2.

$^1$H NMR (CDCl$_3$), δ (ppm): 8.41 (d, J=6.0 Hz, 2H), 7.42–7.46 (m, 6H), 7.33–7.36 (m, 2H), 6.92 (d, J=8.7 Hz, 2H), 4.01–4.06 (m, 2H), 3.74–3.80 (m, 2H), 3.48–3.54 (m, 2H), 3.54–3.42 (m, 2H), 1.77–1.91 (m, 2H), 1.65–1.75 (m, 2H), 1.44–1.48 (m, 1H), 1.04 (d, J=6.3 Hz, 3H). MS (EI): m/z 450 (M+H).

EXAMPLE 10

Synthesis of Compound 10 (Method (VIII))

(S)-1-[5-(4'-Chloro-biphenyl-4-yloxy)-3-methyl-pentyl]-3-pyridin-4-yl-imidazolidin-2-one

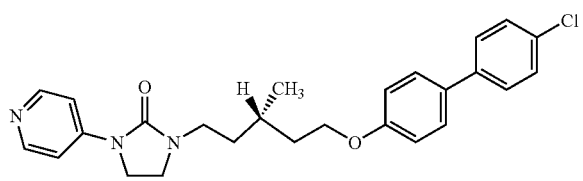

Compound 10 was prepared in a similar manner as described in Example 2.

$^1$H NMR (CDCl$_3$), δ (ppm): 8.41 (d, J=6.0 Hz, 2H), 7.42–7.46 (m, 6H), 7.33–7.36 (m, 2H), 6.92 (d, J=8.7 Hz, 2H), 4.01–4.06 (m, 2H), 3.74–3.80 (m, 2H), 3.48–3.54 (m, 2H), 3.54–3.42 (m, 2H), 1.77–1.91 (m, 2H), 1.65–1.75 (m, 2H), 1.44–1.48 (m, 1H), 1.04 (d, J=6.3 Hz, 3H). MS (EI): m/z 450 (M+H).

EXAMPLE 11

Synthesis of Compound 11 (Method (I))

1-{3-[2-(4'-Chloro-biphenyl-4-yloxy)-ethyl]-4-methyl-pentyl}-3-pyridin-4-yl-imidazolidin-2-one

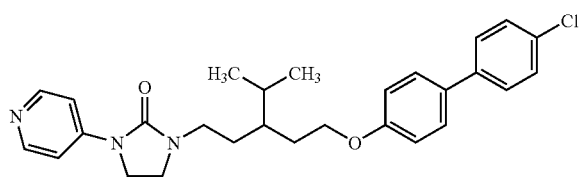

Compound 11 was prepared in a similar manner as described in Example 2.

$^1$H NMR (CDCl$_3$), δ (ppm): 8.40 (d, J=6 Hz, 2H), 7.40–7.45 (m, 6H), 7.34–7.37 (m, 2H), 6.91–6.93 (d, J=8.7 Hz, 2H), 4.02 (t, J=6.6 Hz, 2H), 3.71–3.76 (m, 2H), 3.49–3.54 (m, 2H), 3.35 (t, J=7.2 Hz, 2H), 1.83–1.87 (m, 2H), 1.66–1.73 (m, 2H), 1.49–1.54 (m, 2H), 0.91 (d, J=6.6 Hz, 6H). MS (EI): m/z 478 (M+H).

EXAMPLE 12

Synthesis of Compound 12 (Method (I))

1-[3-Benzyl-5-(4'-chloro-biphenyl-4-yloxy)-pentyl]-3-pyridin-4-yl-imidazolidin-2-one

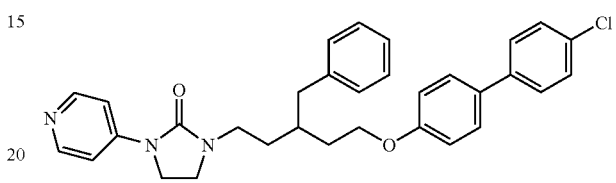

Compound 12 was prepared in a similar manner as described in Example 2.

$^1$H NMR (CDCl$_3$), δ (ppm): 8.41 (dd, J=5.1, 1.2 Hz, 2H), 7.34–7.45 (m, 8H), 7.16–7.29 (m, 5H), 6.90 (d, J=8.7 Hz, 2H), 4.05 (t, J=6.3 Hz, 2H), 3.64–3.70 (m, 2H), 3.31–3.41 (m, 2H), 3.21–3.30 (m, 2H), 2.61–2.76 (m, 2H), 1.94–2.03 (m, 1H), 1.84–1.90 (m, 2H), 1.57–1.64 (m, 2H). MS (EI): m/z 526 (M+H).

EXAMPLE 13

Synthesis of Compound 13 (Method (III))

1-{5-[4-(5-Ethyl-[1,2,4]oxadiazol-3-yl)-phenoxy]-3-methyl-pentyl}-3-pyridin-4-yl-imidazolidin-2-one

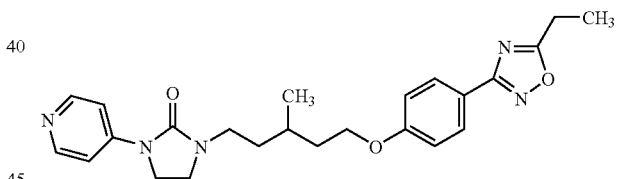

A mixture of 4-[3-methyl-5-(2-oxo-3-pyridin-4-yl-imidazolidin-1-yl)-pentyloxy]-benzonitrile (0.36 g, 1.0 mmol), absolute ethanol (30 mL), finely ground potassium carbonate (0.69 g, 5.0 mmol), and hydroxylamine hydrochloride (0.35 g, 5.0 mmol) was refluxed for 18 h. The hot reaction mixture was filtered, and the remaining solids were washed with hot ethanol. The combined filtrates were concentrated in vacuo to provide amidoxime (0.26 g, 65%). Then to a solution of N-hydroxy-4-[3-methyl-5-(2-oxo-3-pyridin-4-yl-imidazolidin-1-yl)-pentyloxy]-benzamidine (0.26 g, 0.65 mmol) in dry pyridine (10 ml) was added 2.0 equiv of propionyl chloride (0.12 g, 1.30 mmol) at a rate to maintain a gentle reflux. The reaction mixture was refluxed for an additional 0.5–18 h. And then the reaction was quenched with a saturated aqueous ammonium chloride solution followed by extraction with ethyl acetate (100 mL×3). The organic layers were combined and washed with brine, dried over magnesium sulfate, and concentrated under reduced pressure. The crude mixture thus obtained was purified with gradient column chromatography [ethyl acetate and methanol (6:1)] to yield Compound 13 as a white solid (0.19 g, 68%).

¹H NMR (CDCl₃), δ (ppm): 8.40 (br, 2H), 7.95 (d, J=9.0 Hz, 2H), 7.44 (d, J=6.0 Hz, 2H), 6.93 (d, J=9.0 Hz, 2H), 4.01–4.08 (m, 2H), 3.74–3.79 (m, 2H), 3.47–3.53 (m, 2H), 3.33–3.41 (m, 2H), 2.94 (q, J=7.6 Hz, 2H), 1.76–1.93 (m, 2H), 1.62–1.74 (m, 2H), 1.41–1.48 (m, 1H), 1.43 (t, J=7.6 Hz, 3H), 1.03 (d, J=6.3 Hz, 3H). MS (EI): m/z 436 (M+H).

EXAMPLE 14

Synthesis of Compound 14 (Method (III))

1-{3-Methyl-5-[4-(5-trifluoromethyl-[1,2,4]oxadiazol-3-yl)-phenoxy]-pentyl}-3-pyridin-4-yl-imidazolidin-2-one

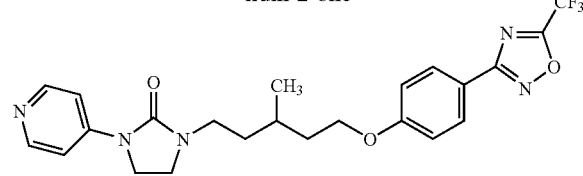

A mixture of 4-[3-methyl-5-(2-oxo-3-pyridin-4-yl-imidazolidin-1-yl)-pentyloxy]-benzonitrile (0.36 g, 1.0 mmol), absolute ethanol (30 mL), finely divided potassium carbonate (0.69 g, 5.0 mmol), and hydroxylamine hydrochloride (0.35 g, 5.0 mmol) was refluxed for 18 h. The hot mixture was filtered, and the remaining solids were washed with hot ethanol. The combined filtrates were concentrated in vacuo to provide the corresponding amidoxime (0.26 g, 65%). Then to a solution of N-hydroxy-4-[3-methyl-5-(2-oxo-3-pyridin-4-yl-imidazolidin-1-yl)-pentyloxy]-benzamidine (0.26 g, 0.65 mmol) in dry pyridine (10 ml) was added 2.0 equiv of trifluoroacetic anhydride (0.27 g, 1.30 mmol) at a rate to maintain a gentle reflux. The reaction mixture was refluxed for an additional 0.5–18 h. And then the reaction was quenched with a saturated aqueous ammonium chloride solution followed by extraction with ethyl acetate (100 mL×3). The organic layers were combined and washed with brine, dried over magnesium sulfate, and concentrated under reduced pressure. The crude mixture thus obtained was purified with gradient chromatography [a mixture of ethyl acetate and methanol (4:1)] to yield Compound 14 as a white solid (0.19 g, 68%).

¹H NMR (CDCl₃), δ (ppm): 8.41 (br, 2H), 8.00 (d, J=9.0 Hz, 2H), 7.45 (d, J=6.3 Hz, 2H), 6.96 (d, J=9.0 Hz, 2H), 4.04–4.09 (m, 2H), 3.75–3.90 (m, 2H), 3.49–3.54 (m, 2H), 3.34–3.41 (m, 2H), 1.81–1.94 (m, 2H), 1.65–1.74 (m, 2H), 1.43–1.50 (m, 1H), 1.04 (d, J=6.3 Hz, 3H). MS (EI): m/z 476 (M+H).

EXAMPLE 15

Synthesis of Compound 15 (Method (I))

1-(2-{[2-(4'-Chloro-biphenyl-4-yloxy)-ethyl]-methyl-amino}-ethyl)-3-pyridin-4-yl-imidazolidin-2-one

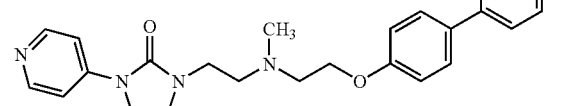

A suspension of 1-(4-pyridyl)-2-imidazolidinone (0.10 g, 0.61 mmol) and sodium hydride (75% dispersion in mineral oil, 0.02 g, 0.67 mmol) in anhydrous DMF (7 mL) was cooled in an ice bath and stirred at 0° C. for 30 minutes, followed by addition of a solution of [2-(4'-chloro-biphenyl-4-yloxy)-ethyl]-(2-chloro-ethyl)-methyl-amine (0.20 g, 0.61 mmol) in anhydrous DMF (5 mL). After 5 minutes, the ice bath was removed and the reaction mixture was stirred at room temperature for 12 hours. The reaction mixture was quenched with water followed by extraction with ethyl acetate (100 mL×3). The organic layers were combined and washed with brine, dried over magnesium sulfate, and concentrated under reduced pressure. The crude mixture thus obtained was purified with flash column chromatography [a mixture of dichloromethane and methanol (6:1)] to yield Compound 15 as a white solid (0.176 g, 64%).

¹H NMR (CDCl₃), δ (ppm): 8.37 (br, 2H), 7.32–7.42 (m, 8H), 6.90 (d, J=8.7 Hz, 2H), 4.06 (t, J=5.3 Hz, 2H), 3.61–3.68 (m, 4H), 3.42 (t, J=6.4 Hz, 2H), 2.86 (t, J=5.3 Hz, 2H), 2.70 (t, J=6.4 Hz, 2H), 2.40 (s, 3H). MS (EI): m/z 451 (M+H).

EXAMPLE 16

Synthesis of Compound 16 (Method (I))

1-(2-{Benzyl-[2-(4'-chloro-biphenyl-4-yloxy)-ethyl]-amino}-ethyl)-3-pyridin-4-yl-imidazolidin-2-one

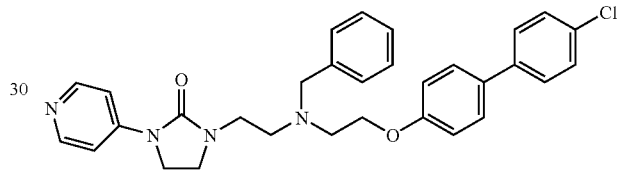

Compound 16 was prepared in a similar manner as described in Example 15.

¹H NMR (CDCl₃), δ (ppm): 8.36 (d, J=5.1 Hz, 2H), 7.25–7.41 (m, 13H), 6.86 (d, J=8.4 Hz, 2H), 4.06 (t, J=5.3 Hz, 2H), 3.73 (s, 2H), 3.50–3.55 (m, 2H), 3.34–3.43 (m, 4H), 2.95 (t, J=5.3 Hz, 2H), 2.78 (t, J=5.9 Hz, 2H). MS (EI): m/z 527 (M+H).

EXAMPLE 17

Synthesis of Compound 17 (Method (I))

1-{2-[[2-(4'-Chloro-biphenyl-4-yloxy)-ethyl]-(4-methyl-benzyl)-amino]-ethyl}-3-pyridin-4-yl-imidazolidin-2-one

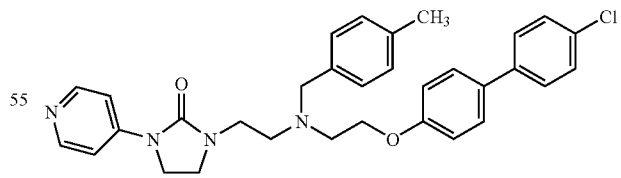

Compound 17 was prepared in a similar manner as described in Example 15.

¹H NMR (CDCl₃), δ (ppm): 8.38 (dd, J=5.0, 1.3 Hz, 2H), 7.34–7.42 (m, 8H), 7.19 (d, J=7.8 Hz, 2H), 7.05 (d, J=7.8 Hz, 2H), 6.88 (d, J=8.7 Hz, 2H), 4.06 (t, J=5.4 Hz, 2H), 3.70 (s, 2H), 3.52–3.53 (m, 2H), 3.48–3.50 (m, 2H), 3.37 (t, J=5.7 Hz, 2H), 2.95 (t, J=5.4 Hz, 2H), 2.79 (t, J=5.7 Hz, 2H), 2.27 (s, 3H). MS (EI): m/z 541 (M+H).

EXAMPLE 18

Synthesis of Compound 18 (Method (I))

1-(2-{(4-Chloro-benzyl)-[2-(4'-chloro-biphenyl-4-yloxy)-ethyl]-amino}-ethyl)-3-pyridin-4-yl-imidazolidin-2-one

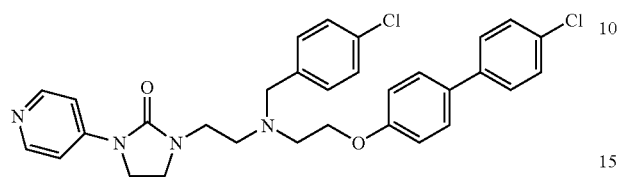

Compound 18 was prepared in a similar manner as described in Example 15.

$^1$H NMR (CDCl$_3$), δ (ppm): 8.41 (dd, J=5.1, 1.2 Hz, 2H), 7.29–7.44 (m, 6H), 7.22–7.29 (m, 6H), 6.89 (d, J=8.7 Hz, 2H), 4.08 (t, J=5.3 Hz, 2H), 3.74 (s, 2H), 3.56–3.61 (m, 2H), 3.44–3.48 (m, 2H), 3.40 (t, J=5.9 Hz, 2H), 2.97 (t, J=5.3 Hz, 2H), 2.81 (t, J=5.9 Hz, 2H). MS (EI): m/z 561 (M+H).

EXAMPLE 19

Synthesis of Compound 19 (Method (I))

1-[6-(4'-Chloro-biphenyl-4-yloxy)-hex-3-enyl]-3-pyridin-4-yl-imidazolidin-2-one

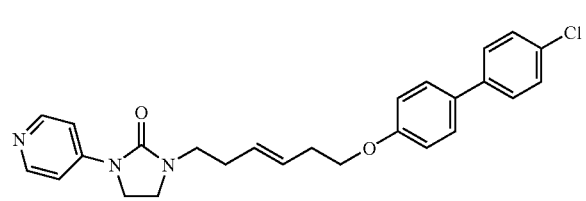

Compound 19 was prepared in a similar manner as described in Example 2.

$^1$H NMR (CDCl$_3$), δ (ppm): 8.37 (br, 2H), 7.32–7.44 (m, 8H), 6.85 (d, J=8.1 Hz, 2H), 5.50–5.66 (m, 2H), 3.94 (t, J=6.3 Hz, 2H), 3.65–3.70 (m, 2H), 3.47–3.52 (m, 2H), 3.35 (t, J=6.8 Hz, 2H), 2.45–2.51 (m, 2H), 2.27–2.33 (m, 2H). MS (EI): m/z 448 (M+H).

EXAMPLE 20

Synthesis of Compound 20 (Method (VII))

1-{3-Methyl-5-[4-(2-methyl-2H-tetrazol-5-yl)-phenoxy]-pentyl}-3-pyridin-4-yl-imidazolidin-2-one

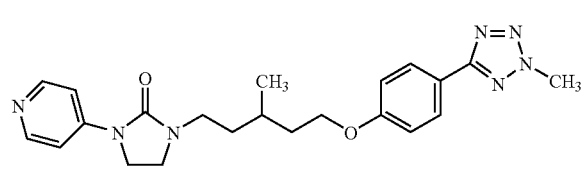

Compound 20 was prepared in a similar manner as described in Example 1.

$^1$H NMR (CDCl$_3$), δ (ppm): 8.41 (br, 2H), 8.01 (d, J=9.0 Hz, 2H), 7.45 (d, J=5.4 Hz, 2H), 6.95 (d, J=9.0 Hz, 2H), 4.36 (s, 3H), 4.03–4.10 (m, 2H), 3.74–3.80 (m, 2H), 3.42–3.54 (m, 2H), 3.34–3.39 (m, 2H), 1.79–1.92 (m, 2H), 1.64–1.73 (m, 2H), 1.40–1.51 (m, 1H), 1.04 (d, J=6.3 Hz, 3H). MS (EI): m/z 422 (M+H).

EXAMPLE 21

Synthesis of Compound 21 (Method (VII))

1-{5-[4-(2-Ethyl-2H-tetrazol-5-yl)-phenoxy]-3-methyl-pentyl}-3-pyridin-4-yl-imidazolidin-2-one

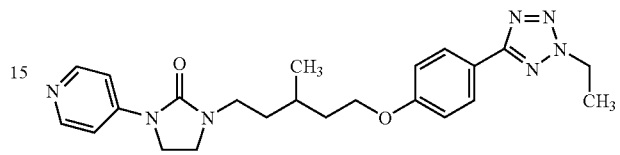

Compound 21 was prepared in a similar manner as described in Example 1.

$^1$H NMR (CDCl$_3$), δ (ppm): 8.36 (d, J=6.3 Hz, 2H), 7.98 (d, J=8.7 Hz, 2H), 7.40 (d, J=6.3 Hz, 2H), 6.91 (d, J=8.7 Hz, 2H), 4.02 (q, J=7.3 Hz, 2H), 3.99–4.04 (m, 2H), 3.68–3.73 (m, 2H), 3.41–3.48 (m, 2H), 3.26–3.39 (m, 2H), 1.67–1.88 (m, 4H), 1.62 (t, J=7.3 Hz, 3H), 1.38–1.47 (m, 1H), 1.00 (d, J=6.3 Hz, 3H). MS (EI): m/z 436 (M+H).

EXAMPLE 22

Synthesis of Compound 22 (Method (I))

1-[5-(4'-Chloro-biphenyl-4-yloxy)-3-trifluoromethyl-pentyl]-3-pyridin-4-yl-imidazolidin-2-one

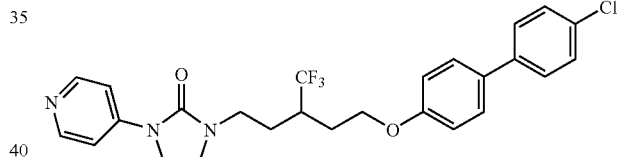

Compound 22 was prepared in a similar manner as described in Example 2.

$^1$H NMR (CDCl$_3$), δ (ppm): 8.39 (d, J=6.3 Hz, 2H), 7.33–7.42 (m, 8H), 6.90 (d, J=8.7 Hz, 2H), 4.07–4.11 (m, 2H), 3.64–3.71 (m, 2H), 3.35–3.54 (m, 4H), 2.49–2.52 (m, 1H), 2.18–2.45 (m, 1H), 1.91–2.00 (m, 2H), 1.77–1.84 (m, 1H). MS (EI): m/z 504 (M+H).

EXAMPLE 23

Synthesis of Compound 23 (Method (I))

1-{5-[4-(5-Chloro-thiophen-2-yl)-phenoxy]-3-methyl-pentyl}-3-pyridin-4-yl-imidazolidin-2-one

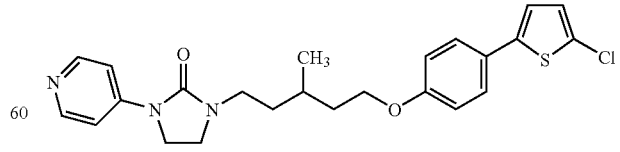

Compound 23 was prepared in a similar manner as described in Example 1.

$^1$H NMR (CDCl$_3$), δ (ppm): 8.41 (d, J=5.1 Hz, 2H), 7.45 (d, J=6.0 Hz, 2H), 7.37 (d, J=8.7 Hz, 2H), 6.82–6.92 (m, 4H), 3.99–4.04 (m, 2H), 3.74–3.79 (m, 2H), 3.48–3.53 (m, 2H), 3.33–3.43 (m, 2H), 1.81–1.90 (m, 2H), 1.63–1.76 (m, 2H), 1.41–1.47 (m, 1H), 1.03 (d, J=6.3 Hz, 3H). MS (EI): m/z 456 (M+H).

EXAMPLE 24

Synthesis of Compound 24 (Method (I))

1-[4-(4'-Chloro-biphenyl-4-yloxymethyl)-benzyl]-3-pyridin-4-yl-imidazolidin-2-one

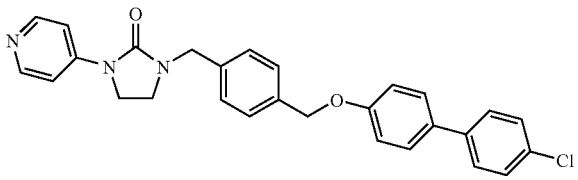

Compound 24 was prepared in a similar manner as described in Example 1.

$^1$H NMR (CDCl$_3$), δ (ppm): 8.44 (d, J=6.0 Hz, 2H), 7.54 (d, J=6.3 Hz, 2H), 7.42–7.48 (m, 6H), 7.24–7.37 (m, 4H), 7.02 (d, J=8.7 Hz, 2H), 5.10 (s, 2H), 4.52 (s, 2H), 3.78–3.83 (m, 2H), 3.41–3.46 (m, 2H). MS (EI): m/z 470 (M+H).

EXAMPLE 25

Synthesis of Compound 25 (Method (I))

1-[3-(4'-Chloro-biphenyl-4-yloxymethyl)-benzyl]-3-pyridin-4-yl-imidazolidin-2-one

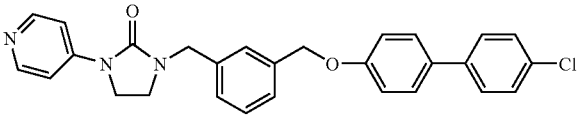

Compound 25 was prepared in a similar manner as described in Example 1.

$^1$H NMR (CDCl$_3$), δ (ppm): 8.43 (br, 2H), 7.42–7.52 (m, 6H), 7.34–7.39 (m, 6H), 7.0 (d, J=8.7 Hz, 2H), 5.09 (s, 2H), 4.51 (s, 2H), 3.75–3.81 (m, 2H), 3.39–3.44 (m, 2H). MS (EI): m/z 470 (M+H).

EXAMPLE 26

Synthesis of Compound 26 (Method (I))

1-[2-(4'-Chloro-biphenyl-4-yloxymethyl)-benzyl]-3-pyridin-4-yl-imidazolidin-2-one

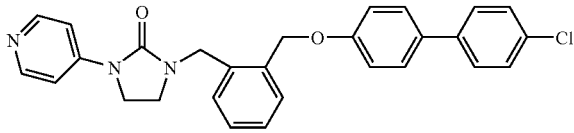

Compound 26 was prepared in a similar manner as described in Example 1.

$^1$H NMR (CDCl$_3$), δ (ppm): 8.22 (br, 2H), 7.25–7.41 (m, 12H), 6.85 (d, J=8.7 Hz, 2H), 4.99 (s, 2H), 4.52 (s, 2H), 3.59–3.64 (m, 2H), 3.27–3.32 (m, 2H). MS (EI): m/z 470 (M+H).

EXAMPLE 27

Synthesis of Compound 27 (Method (I))

1-[3-(4'-Chloro-biphenyl-4-yloxymethyl)-5-methyl-benzyl]-3-pyridin-4-yl-imidazolidin-2-one

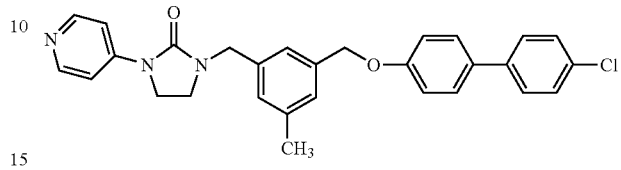

Compound 27 was prepared in a similar manner as described in Example 1.

$^1$H NMR (CDCl$_3$), δ (ppm): 8.43 (d, J=6.0 Hz, 2H), 7.34–7.49 (m, 7H), 7.17 (d, J=15.0 Hz, 2H), 7.04 (d, J=15.0 Hz, 2H), 7.0 (d, J=8.4 Hz, 2H), 5.04 (s, 2H), 4.45 (s, 2H), 3.73–3.78 (m, 2H), 3.36–3.42 (m, 2H), 2.37 (s, 3H). MS (EI): m/z 484 (M+H).

EXAMPLE 28

Synthesis of Compound 28 (Method (I))

1-[6-(4'-Chloro-biphenyl-4-yloxymethyl)-pyridin-2-ylmethyl]-3-pyridin-4-yl-imidazolidin-2-one

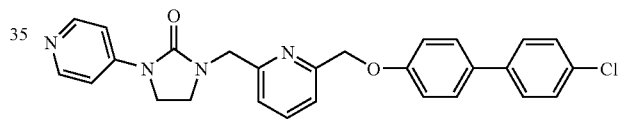

Compound 28 was prepared in a similar manner as described in Example 1.

$^1$H NMR (CDCl$_3$), δ (ppm): 8.44 (d, J=6.3 Hz, 2H), 7.25–7.74 (m, 11H), 7.02 (d, J=8.7 Hz, 2H), 5.21 (s, 2H), 4.62 (s, 2H), 3.79–3.85 (m, 2H), 3.58–3.63 (m, 2H). MS(ED): m/z 471 (M+H).

EXAMPLE 29

Synthesis of Compound 29 (Method (I))

1-[5-(4'-Chloro-biphenyl-4-yloxy)-1-methyl-pentyl]-3-pyridin-4-yl-imidazolidin-2-one

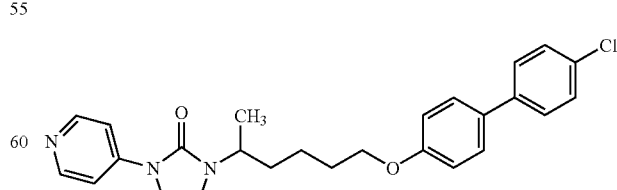

Compound 29 was prepared in a similar manner as described in Example 6.

MS(EI): m/z 450 (M+H).

EXAMPLE 30

Synthesis of Compound 30 (Method (II))

1-[5-(4'-Chloro-biphenyl-4-yloxy)-hexyl]-3-pyridin-4-yl-imidazolidin-2-one

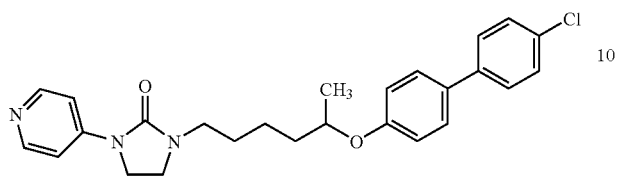

Compound 30 was prepared in a similar manner as described in Example 7.

$^1$H NMR (CDCl$_3$), δ (ppm): 8.41 (d, J=6.0 Hz, 2H), 7.41–7.46 (m, 6H), 7.32–7.37 (m, 2H), 6.91 (d, J=9.0 Hz, 2H), 4.36–4.42 (m, 1H), 3.74–3.80 (m, 2H), 3.47–3.53 (m, 2H), 3.29–3.33 (m, 2H), 1.78–1.83 (m, 2H), 1.59–1.75 (m, 2H), 1.41–1.56 (m, 2H), 1.32 (d, J=6.0 Hz, 3H). MS(EI): m/z 450 (M+H).

EXAMPLES 31–103

Synthesis of Compounds 31–103

Each of Compounds 31–103 was prepared by one of Methods (I)–(IX).

EXAMPLE 104

In vitro Antiviral Activity Against Enterovirus

Enterovirus 71 (EV71) isolates were obtained from Chang Gung Children's Hospitals (Taipei, Taiwan) and National Cheng Kung University Hospital (Tainan, Taiwan). BrCr, the prototype of EV71, was obtained from the American Type Culture Collection (ATCC Accession No. VR 784). EV71-2231 and EV71-1743 were isolated from throat swabs, while EV71-2272 was isolated from the spinal cord of a fatal case. EV71-2086 was isolated from the skin lesion of an implicated HFMD (hand, foot, and mouth disease) patient. EV71-4643 was a clinical isolate obtained from the throat swabs of an 18-month-old patient with encephalitis. MRC-5 cells (ATCC Accession No. CCL-171) and vero cells (ATCC Accession No. CCL-81) were used for virus isolation and propagation.

The antiviral activity of a number of imidazolidinone compounds was determined by a standard plaque reduction assay as described in Otto et al., Antimicrobial Agents & Chemotherapy, 1985, 27:883–886.

More specifically, vero cells in monolayers were infected at a virus concentration to give approximately 50–100 plaques per monolayer in the virus control (without a test compound). A compound to be tested was serially diluted and included in the agar-medium overlay. Plates were incubated at 35° C. for 96 hours. The plaques were stained with crystal violet and counted. IC$_{50}$, the concentration at which a tested compound reduced the number of plaques by 50% with respect to the untreated virus control, was then determined.

A number of compounds were tested against some of the serotypes from either a panel of four human enterovirus serotypes (namely, EV68, EV71-2086, EV71-2231, EV71-BrCr, and EV71-1743), or a panel of human coxsackievirus serotypes (namely, COX-A16, -A9, -A10, -A24, -B1, -B2, -B3, -B4, -B5, and -B6), or echovirus (-9 and -29), human rhinovirus-14, HSV-1, influenza A (WSN), and influenza B (HK). The efficacy of each compound was determined in terms of IC$_{50}$, which was the concentration of the compound required to inhibit 50% of the tested virus.

All of the tested compounds (i.e., Compounds 1, 6, 7, 9, 10, 13, 14, 20, 21, 22, 23, 29, and 30) showed antiviral activity against enterovirus, in particular, EV71, coxsackieviruses A9, and A24.

EXAMPLE 105

In vivo Antiviral Activity Against EV71

A mouse-adapted EV71 strain 4643 MP4 was kindly provided by Professor Lei, Huan-Yao at the Department of Microbiology and Immunology of the National Cheng Kung University, Tainan, Taiwan. 4643 MP4 was propagated in rhabdomyosarcoma cells (RD) in DMEM supplemented with 2% fetal bovine serum. The virus titer expressed in plaque formation unit (PFU) was determined by plaque assay on RD cells based on a typical cytopathic effect. A virus stock with a titer of 1.5×10$^7$ PFU/ml was collected and kept at −80° C. for further animal studies.

ICR neonatal mice of 2 day old were intraperitoneally inoculated each with EV71 of 435 PFU in 50 µl, which caused an optimal mortality of 70–90% infected mice within a 2-week observation period. Each of test compounds was suspended in 0.5% methyl-cellulose. The virus-inoculated neonatal mice were orally gavaged with 10 µl of the test compounds or the formulation vehicle as a negative control. Different regimens were explored to show the activity of the test compounds, i.e., 10 to 200 mg/kg; before and/or after the inoculation; and daily treatments for a week. The mice were examined daily and the mortality of treated and control groups were recorded. The test results showed that the infected mice treated with a test compound had significantly greater survival rate than the negative control mice.

OTHER EMBODIMENTS

A number of embodiments of the invention have been described. Nevertheless, it will be understood that various modifications may be made without departing from the spirit and scope of the invention. Other aspects, advantages and modifications within the scope of this invention will be apparent to those skilled in the art to which this invention pertains. Accordingly, other embodiments are within the scope of the following claims:

What is claimed is:

1. A compound of the following formula:

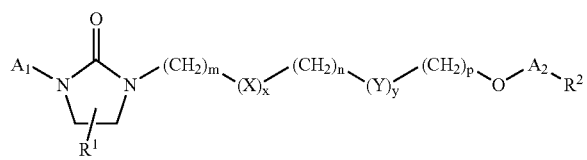

wherein
each of R$^1$ and R$^2$, independently, is H, halo, C$_{1-5}$ alkyl, C$_{1-5}$ haloalkyl, C$_{6-12}$ aryl, C$_{6-12}$ aralkyl, or heteroaryl, optionally substituted with halo, —OR$^a$, C$_{1-5}$ alkyl, substituted aryl, substituted heteroaryl, C$_{1-5}$ haloalkyl, C$_{1-5}$ alkyl-OR$^a$, —CN, —C(O)R$^a$, —SR$^a$, —S(O)R$^a$, —S(O)$_2$R$^a$, —NR$^a$R$^{a'}$, —C(O)OR$^a$, —C(O)NR$^a$R$^{a'}$, —NO$_2$, —OC(O)R$^a$, —NR$^a$C(O)R$^{a'}$, —NR$^a$C(O)OR$^{a'}$, or —NR$^a$C(O)NR$^a$'R$^{a''}$; in which each of R$^a$, R$^{a'}$, and R$^{a''}$, independently, is H, C$_{1-5}$ alkyl, or aryl;

each of $A_1$ and $A_2$, independently, is $C_{6-12}$ aryl, $C_{6-12}$ aralkyl, or heteroaryl, optionally substituted with halo, —$OR^b$, $C_{1-5}$ alkyl, $C_{1-5}$ haloalkyl, $C_{1-5}$ alkyl-$OR^b$, —CN, —$NO_2$, —C(O)$R^b$, —$SR^b$, —S(O)$R^b$, —S(O)$_2$$R^b$, —$NR^bR^{b'}$, —C(O)$OR^b$, —C(O)$NR^bR^{b'}$, —$NO_2$, —OC(O)$R^{b'}$, —$NR^bC(O)R^{b'}$, —$NR^bC(O)OR^{b'}$, or —$NR^bC(O)NR^{b'}R^{b''}$, provided that if $A_1$ is heteroaryl, it forms a C—N bond with the imidazolidinone ring; in which each of $R^b$, $R^{b'}$, and $R^{b''}$, independently, is H, $C_{1-5}$ alkyl, or aryl;

each of X and Y, independently, is —C(H)($R^c$)—, —C($R^c$)($R^{c'}$)—, —$NR^{c''}$—, —S—, —S(O)—, —S(O)$_2$—, —C(H)(O$R^d$)—, —C(H)[OC(O)$R^d$]—, —C(H)(N$R^dR^{d'}$)—, —C(H)[N$R^dC(O)R^{d'}$]—, —C(H)[N$R^dC(O)OR^{d'}$], —C(H)[N$R^dC(O)NR^{d'}R^{d''}$], —C(H)(SH)—, —C(H)(S$R^d$)—, —C(H)(SO$R^d$)—, —C(H)(SO$_2R^d$)—, $C_{6-12}$ aryl, cyclyl, heterocyclyl, heteroaryl, alkenyl, alkynyl,

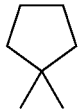

or

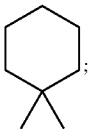

in which each of $R^c$ and $R^{c'}$, independently, is halo, $C_{1-5}$ alkyl, $C_{1-5}$ haloalkyl, $C_{1-5}$ hydroxyalkyl, $C_{1-5}$ aminoalkyl, $C_{1-5}$ alkoxy, $C_{1-5}$ aryloxy, $C_{6-12}$ aryl, $C_{6-12}$ aralkyl, or heteroaryl; $R^{c''}$ is $C_{1-5}$ alkyl, $C_{1-5}$ haloalkyl, $C_{1-5}$ hydroxyalkyl, $C_{1-5}$ aminoalkyl, $C_{6-12}$ aryl, $C_{6-12}$ aralkyl, or heteroaryl; and each of $R^d$, $R^{d'}$, and $R^{d''}$, independently, is H, $C_{1-5}$ alkyl, or aryl;

each of m, n, and p, independently, is 0, 1, 2, 3, 4, or 5; and each of x and y, independently, is 0 or 1, provided that at least one of x and y is 1.

2. The compound of claim 1, wherein x is 1, y is 0, and p is 0.

3. The compound of claim 2, wherein $R^1$ is H.

4. The compound of claim 3, wherein $A_1$ is pyridin-4-yl.

5. The compound of claim 4, wherein $A_2$ is aryl.

6. The compound of claim 5, wherein $A_2$ is phenyl.

7. The compound of claim 6, wherein $R^2$ is substituted at position 4 of phenyl.

8. The compound of claim 7, wherein $R^2$ is $C_{6-12}$ aryl or heteroaryl, optionally substituted with halo, $C_{1-5}$ alkyl, or $C_{1-5}$ haloalkyl.

9. The compound of claim 8, wherein X is —C(H)($R^c$)—, —C($R^c$)($R^{c'}$)—, —$NR^{c''}$—, or phenyl.

10. The compound of claim 9, wherein X is —C(H)(CH$_3$)—.

11. The compound of claim 10, wherein $R^2$ is phenyl, 1,2,4-oxadiazolyl, tetrazolyl, or thienyl, optionally substituted with halo or $C_{1-5}$ alkyl.

12. The compound of claim 11, wherein $R^2$ is 4-chlorophenyl, 4-fluorophenyl, 2,4-dichlorophenyl, 5-methyl-1,2,4-oxadiazolyl, 5-ethyl-1,2,4-oxadiazolyl, 3-ethyl-tetrazolyl, or 5-chlorothien-2-yl.

13. The compound of claim 12, wherein the sum of m and n is 4.

14. The compound of claim 9, wherein X is —C(CH$_3$)(CH$_3$)—.

15. The compound of claim 14, wherein $R^2$ is phenyl, 1,2,4-oxadiazolyl, tetrazolyl, or thienyl, optionally substituted with halo or $C_{1-5}$ alkyl.

16. The compound of claim 15, wherein $R^2$ is 4-chlorophenyl, 4-fluorophenyl, 2,4-dichlorophenyl, 5-methyl-1,2,4-oxadiazolyl, 5-ethyl-1,2,4-oxadiazolyl, 3-ethyl-tetrazolyl, or 5-chlorothien-2-yl.

17. The compound of claim 16, wherein the sum of m and n is 4.

18. The compound of claim 9, wherein X is —N(CH$_3$)—.

19. The compound of claim 18, wherein R is phenyl, 1,2,4-oxadiazolyl, tetrazolyl, or thienyl, optionally substituted with halo or $C_{1-5}$ alkyl.

20. The compound of claim 19, wherein $R^2$ is 4-chlorophenyl, 4-fluorophenyl, 2,4-dichlorophenyl, 5-methyl-1,2,4-oxadiazolyl, 5-ethyl-1,2,4-oxadiazolyl, 3-ethyl-tetrazolyl, or 5-chlorothien-2-yl.

21. The compound of claim 20, wherein the sum of m and n is 4.

22. The compound of claim 9, wherein X is phenyl.

23. The compound of claim 22, wherein $R^2$ is phenyl, 1,2,4-oxadiazolyl, tetrazolyl, or thienyl, optionally substituted with halo or $C_{1-5}$ alkyl.

24. The compound of claim 23, wherein $R^2$ is 4-chlorophenyl, 4-fluorophenyl, 2,4-dichlorophenyl, 5-methyl-1,2,4-oxadiazolyl, 5-ethyl-1,2,4-oxadiazolyl, 3-ethyl-tetrazolyl, or 5-chlorothien-2-yl.

25. The compound of claim 24, wherein the sum of m and n is 4.

26. The compound of claim 9, wherein X is —C(H)(CF$_3$)—.

27. The compound of claim 26, wherein $R^2$ is phenyl, 1,2,4-oxadiazolyl, tetrazolyl, or thienyl optionally substituted with halo or $C_{1-5}$ alkyl.

28. The compound of claim 27, wherein $R^2$ is 4-chlorophenyl, 4-fluorophenyl, 2,4-dichlorophenyl, 5-methyl-1,2,4-oxadiazolyl, 5-ethyl-1,2,4-oxadiazolyl, 3-ethyl-tetrazolyl, or 5-chlorothien-2-yl.

29. The compound of claim 28, wherein the sum of m and n is 4.

30. The compound of claim 8, wherein $R^2$ is phenyl optionally substituted with halo.

31. The compound of claim 30, wherein X is —C(H)($R^c$)—, —C($R^c$)($R^{c'}$)—, —$NR^{c''}$—, or phenyl.

32. The compound of claim 31, wherein X is —N(CH$_3$)—, —C(H)(CH$_3$)—, —C(H)(CF$_3$)—, —C(CH$_3$)(CH$_3$)—, or phenyl.

33. The compound of claim 8, wherein X is 1,2,4-oxadiazolyl2,4-oxadiazolyl, tetrazolyl, or thienyl, optionally substituted with halo or $C_{1-5}$ alkyl.

34. The compound of claim 33, wherein X is, —C(H)($R^c$)—, —C($R^c$)($R^{c'}$)—, —$NR^{c''}$— or phenyl.

35. The compound of claim 34, wherein X is —N(CH$_3$)—, —C(H)(CH$_3$)—, —C(H)(CF$_3$)—, —C(CH$_3$)(CH$_3$)—, or phenyl.

36. The compound of claim 1, wherein $A_2$ is phenyl.

37. The compound of claim 36, wherein $R^1$ is H.

38. The compound of claim 37, wherein $A_1$ is pyridin-4-yl.

39. The compound of claim 1, wherein $R^1$ is H.

40. The compound of claim 39, wherein $A_1$ is pyridin-4-yl.

41. The compound of claim 1, wherein the compound is
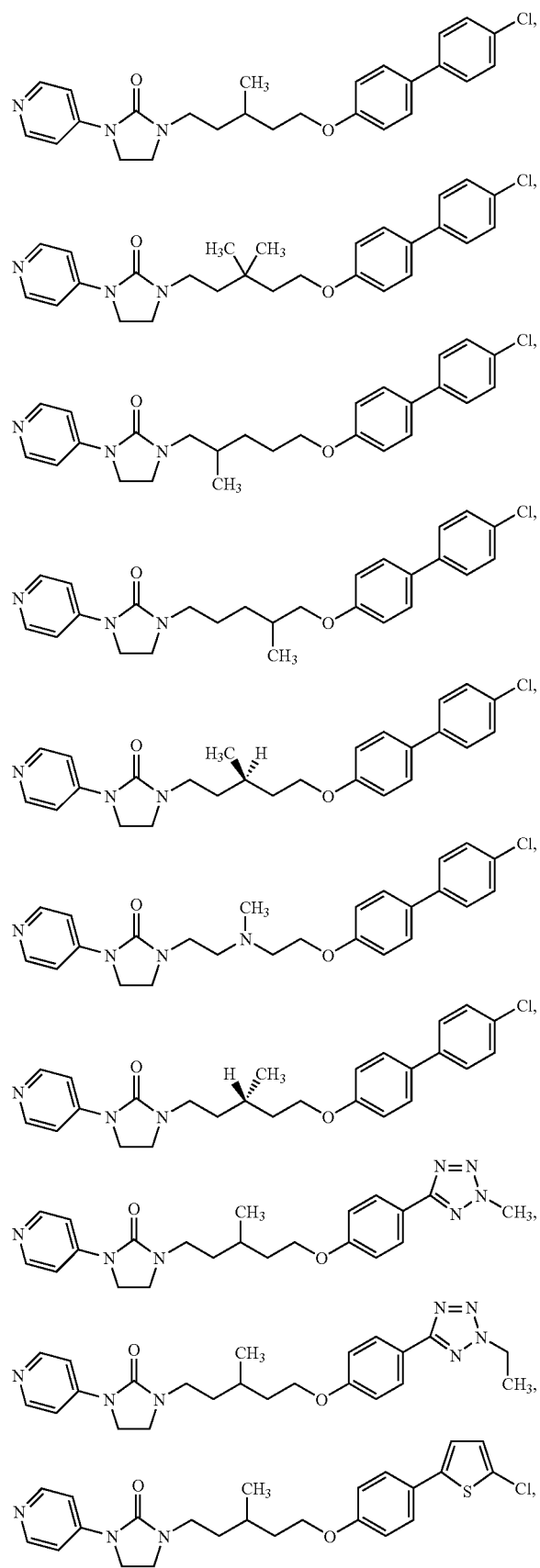
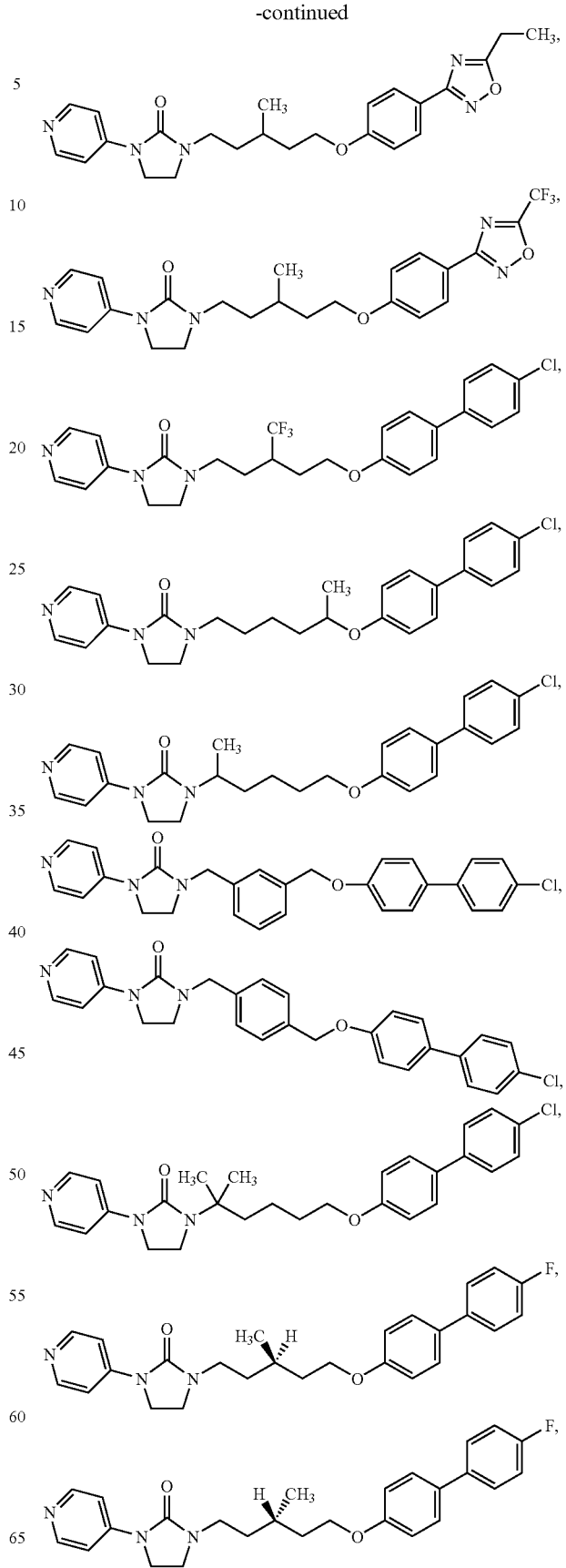

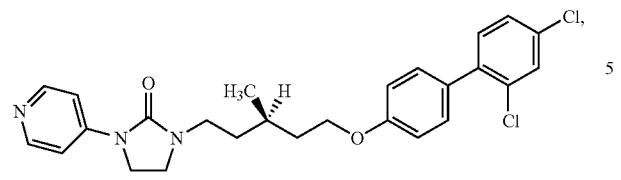
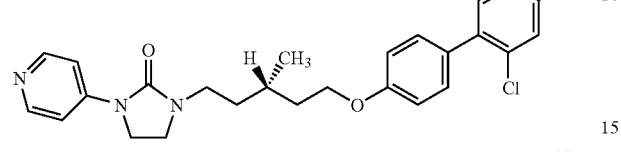
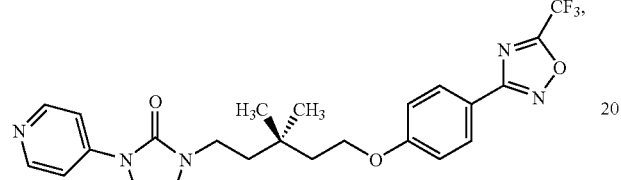
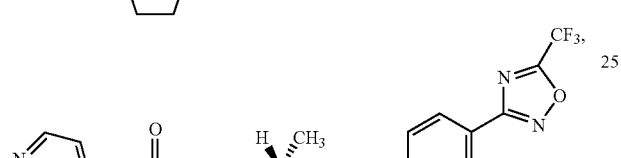
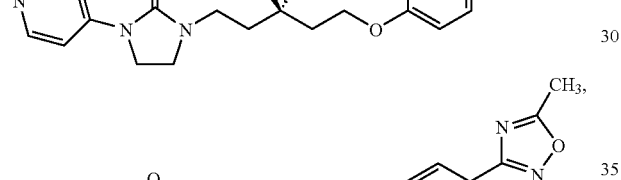
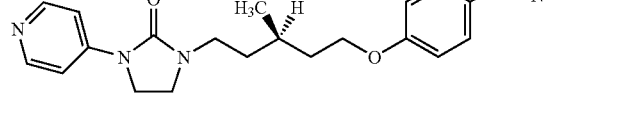
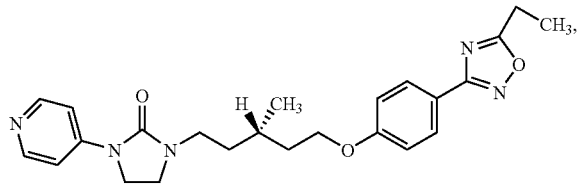
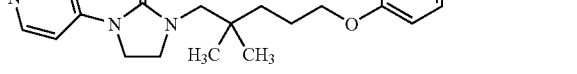
, or
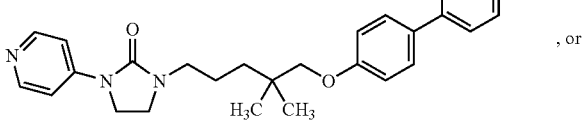
\* \* \* \* \*